United States Patent
Jain et al.

(10) Patent No.: US 11,268,958 B2
(45) Date of Patent: Mar. 8, 2022

(54) BACTERIA-SPECIFIC LABELED SUBSTRTATES AS IMAGING BIOMARKERS TO DIAGNOSE, LOCATE, AND MONITOR INFECTIONS

(71) Applicant: THE JOHNS HOPKINS UNIVERSITY, Baltimore, MD (US)

(72) Inventors: Sanjay K. Jain, Baltimore, MD (US); Martin Gilbert Pomper, Baltimore, MD (US); Edward A. Weinstein, Baltimore, MD (US); Alvaro Ordonez, Baltimore, MD (US); Mariah Klunk, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/427,774

(22) PCT Filed: Sep. 16, 2013

(86) PCT No.: PCT/US2013/059897
§ 371 (c)(1),
(2) Date: Mar. 12, 2015

(87) PCT Pub. No.: WO2014/043606
PCT Pub. Date: Mar. 20, 2014

(65) Prior Publication Data
US 2015/0250906 A1    Sep. 10, 2015

Related U.S. Application Data

(60) Provisional application No. 61/701,041, filed on Sep. 14, 2012, provisional application No. 61/765,925, filed on Feb. 18, 2013.

(51) Int. Cl.
*G01N 33/569* (2006.01)

(52) U.S. Cl.
CPC ... *G01N 33/56944* (2013.01); *G01N 33/5695* (2013.01); *G01N 33/56916* (2013.01); *G01N 33/56938* (2013.01); *G01N 2800/26* (2013.01)

(58) Field of Classification Search
CPC ............ A61K 51/0491; A61K 51/0402; A61K 31/496; A61K 45/06; A61K 47/61; A61K 49/0021; A61K 49/0032; A61K 49/0054; A61K 51/06; A61K 51/065; C08B 31/00; C08L 3/04
See application file for complete search history.

(56) References Cited

U.S. PATENT DOCUMENTS

2008/0193373 A1    8/2008    Stritzker et al.

FOREIGN PATENT DOCUMENTS

KR    10-2008-0083266 A    9/2008
WO    WO 01/25399 A2 *    4/2001

OTHER PUBLICATIONS

Davis et al. PLoS ONE 4(7): e6297, 2009.*
Weinstein et al. Sci. Transl. Med. 6 (259): Oct. 22, 2014.*
Liu et al. Oncol. Lett. 8: 2359-2366, online pub Sep. 11, 2014.*
Zhu et al. J. Nuclear Medicine 56 (suppl. 3), abstract# 1021,2015.*
Li et al. Mol. Imaging Biol. 10: 92-98, 2008.*
Johnson et al. Nucl. Med. Biol. 41: 777-784, 2014.*
Bohsali et al. BMC Microbiol. 10: 237, abstract, 2010.*
Camilo, E., et al., "Folate synthesized by bacteria in human upper small intestine is assimilated by the host", Gastroenterology (1996) vol. 10, pp. 991-998.
Lewis, S., et al., "Improvement in specificity of [14C]d-xylose breath test for bacterial overgrowth", Digestive Diseases and Sciences (1997) vol. 42, No. 8, pp. 1587-1592.
Dukowicz, A., et al., "Small intestinal bacterial overgrowth: a comprehensive review" (2007) Gastroenterololgy & Hepatology, vol. 3, Issue 2, pp. 112-122.
Brugger, S., et al., "Commensal-Pathogen Interactions along the Human Nasal Passages" (2016) PLoS Pathog 12 (7): e1005633. doi:10.1371/journal.ppat.1005633.
Kluytmans, J., et al., "Nasal Carriage of *Staphylococcus aureus*: Epidemiology, Underlying Mechanisms, and Associated Risks" (1997) Clinical Microbiology Reviews, p. 505-520, vol. 10, No. 3.
Mest, D., et al., "Nasal Colonization with Methicillin-Resistant *Staphylococcus aureus* on Admission to the Surgical Intensive Care Unit Increases the Risk of Infection" (1994) Anesth Analg, vol. 78, pp. 644-650.
Mika, M., et al., "Influence of the pneumococcal conjugate vaccines on the temporal variation of pneumococcal carriage and the nasal microbiota in healthy infants: a longitudinal analysis of a case-control study" (2017) Microbiome, vol. 5, No. 85.
Ordonez, A., et al., "A Systematic Approach for Developing Bacteria-Specific Imaging Tracers" (2017) J Nucl Med; 58:144-150.
Perl, T., et al., "New Approaches to Reduce *Staphylococcus aureus* Nosocomial Infection Rates: Treating *S. aureus* Nasal Carriage" Ann Pharmacother (1998) 32(suppl):S7-16.
Perl, T., et al., "Intranasal Mupirocin To Prevent Postoperative *Staphylococcus Aureus* Infections" N Engl J Med, (2002) vol. 346, No. 24.
Perl, T., "Prevention of *Staphylococcus aureus* infections among surgical patients: Beyond traditional perioperative prophylaxis" Surgery (2003) vol. 134, No. 5.

(Continued)

Primary Examiner — Sarvamangala Devi
(74) Attorney, Agent, or Firm — Johns Hopkins Technology Ventures

(57) ABSTRACT

The methods of the present invention exploit unique biochemical pathways present within infectious organisms to develop small molecule metabolic tracers. Labeled substrates created using these inventive methods were created. The labeled substrates can be used to determine whether a subject is infected with an infectious organism by imaging means, and with use of two or more such labeled substrates, methods of differentiating gram negative infection from gram positive infection, and methods of localizing and quantifying infectious disease burden are provided. The methods of the present invention can assist in the clinical decision to begin empiric antibiotic therapy, determine its efficacy, as well as the choice of antibacterial agents.

2 Claims, 14 Drawing Sheets

(56) References Cited

OTHER PUBLICATIONS

Pujol, M., et al., "Nosocomial *Staphylococcus aureus* Bacteremia among Nasal Carriers of Methicillin-resistant and Methicillin-susceptible Strains" The American Journal of Medicine (1996) vol. 100.

Virology Blog: Virus-induced fever might change bacteria from commensal to pathogen: (2013).

Voneiff, C., et al., "Nasal Carriage as a Source of *Staphylococcus aureus* Bacteremia" (2001) N Engl J Med, vol. 344, No. 1.

Wenzel, R., et al., "The significance of nasal carrage of *Staphylococcus aureus* and the incidence of postoperative wound infection" (1995) Journal of Hospital Infection, vol. 31, pp. 13-24.

Yano, M., et al., "Preoperative intranasal mupirocin ointment significantly reduces postoperative infection with *Staphylococcus aureus* in patients undergoing upper gastrointestinal surgery" (2000) Surg Today vol. 30, pp. 16-21.

\* cited by examiner

| COMPOUND | STRUCTURE | TARGET PATHWAY |
|---|---|---|
| p-AMINOBENZOIC ACID (PABA) | 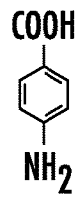 | FOLIC ACID SYNTHESIS |
| rac-2,6-DIAMINOPIMELIC ACID (DAP) | 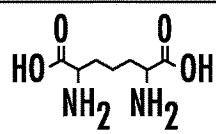 | CELL WALL SYNTHESIS |
| D-XYLOSE (XYL) | 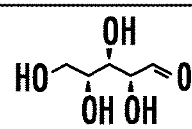 | CARBOHYDRATE METABOLISM |
| METHYL-ALPHA-D-GLUCOPYRANOSIDE (MGP) | 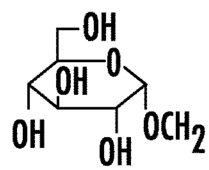 | CARBOHYDRATE METABOLISM |
| SHIKIMATE (SHIK) | 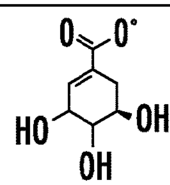 | AROMATIC AMINO ACID SYNTHESIS |
| CELLOBIOSE (CB) | 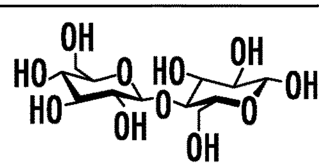 | CARBOHYDRATE METABOLISM |
| MANNITOL (MAN) | 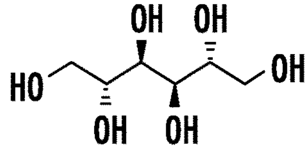 | CARBOHYDRATE METABOLISM |

|  | S. aureus | E. coli | M. smegmatis |
|---|---|---|---|
| PABA | 58% | 25% | 88% |
| MAN | 66% | 82% | 83% |
| DAP | 3% | 49% | 58% |
| XYL | 0% | 74% | 1% |
| MGP | 11% | 27% | 0% |
| SHIK | 0% | 6% | 0% |
| CB | 2% | 1% | 0% |

BACTERIA-SPECIFIC LABELED SUBSTRTATES AS IMAGING BIOMARKERS TO DIAGNOSE, LOCATE, AND MONITOR INFECTIONS

CROSS-REFERENCE TO RELATED APPLICATIONS

This application is a 35 U.S.C. § 371 U.S. national entry of International Application PCT/US2013/059897, having an international filing date of Sep. 16, 2013, which claims the benefit of U.S. Provisional Patent Application Nos. 61/701,041, filed on Sep. 14, 2012, and 61/765,925, filed on Feb. 18, 2013, the content of each of the aforementioned applications is herein incorporated by reference in their entirety.

STATEMENT OF GOVERNMENTAL INTEREST

This invention was made with government support under grant number OD006492 and EB020539, awarded by the National Institutes of Health. The government has certain rights in the invention.

BACKGROUND OF THE INVENTION

Diagnosis of infectious diseases by standard diagnostic tools, namely microscopy and microbiologic culture are often limited due to difficult sampling of obscure or deep sites of infection such as bone, cardiac, central nervous system, pulmonary or intra-abdominal locations. Rapid diagnosis of infectious disease is critical for administering appropriate antibiotic therapy, especially in modern patient populations who may be immunocompromised by HIV infection, solid organ transplant, autoimmune, or cancer chemotherapies. Traditional diagnostic methods are dependent upon sampling suspected sites of infection, then performing culture or molecular techniques. This approach is both labor intensive and time consuming, and is subject to the uncertainties of incorrect sampling and contamination. It may also be dangerous (e.g. brain biopsies or biopsies in patients with bleeding risk) or sometimes impossible (e.g. patients who are at high risk for complications secondary to anesthesia).

Complimentary techniques, such as cross sectional imaging by computed tomography or magnetic resonance imaging may provide a site of interest for invasive tissue sampling, but reveal structural abnormalities which are often a late occurrence in the disease process. Furthermore, normal structure may be perturbed following surgical procedures, and indolent infections may not produce significant morphologic changes. Standard imaging is therefore a lagging indicator, and only by repeated imaging is the success of antimicrobial therapy inferred. Nuclear medicine imaging techniques, such as $^{18}$F-fluorodeoxyglucose positron emission tomography have the potential to noninvasively determine the location and severity of infection as well as the response to therapy, but unfortunately are dependent upon host white blood cell function, and cannot differentiate between cancer, sterile inflammation or infection. As a result, there remains a need for prokaryote specific radiopharmaceutical agents that can rapidly and accurately diagnose and monitor infection.

SUMMARY OF THE INVENTION

The compositions and methods of the present invention exploit unique biochemical pathways present within infectious organisms, such as prokaryotes, to develop a series of small molecule metabolic tracers. Potential imaging agents were selected by three major criteria: 1) Presence of prokaryote specific metabolic pathway 2) Absence of known host metabolism and 3) Evidence for accumulation of tracer or essentiality of the pathway for bacterial survival.

In accordance with an embodiment, the present invention provides a method for detection of the presence of infectious organisms in a mammalian host comprising: a) administering to the host a therapeutically effective amount of a compound comprising a labeled substrate, wherein the substrate is a compound that is solely utilized by the metabolism of the infectious organism selected from the group consisting of prokaryotes, fungi, protozoa, and virally infected host cells; and wherein the label of the labeled substrate is a detectable moiety selected from the group consisting of radionuclides, near-infrared dyes, fluorescent dyes, PET, SPECT and MRI imaging agents; b) allowing a sufficient period of time for the infectious organism to take up the labeled substrate; and c) determining whether the infectious organisms are present in the host by detecting the labeled substrate in the body of the mammalian host.

In accordance with another embodiment, the present invention provides a method for detection of the location of infectious organisms in the body of a mammalian host comprising: a) administering to the host a therapeutically effective amount of a compound comprising a labeled substrate, wherein the substrate is a compound that is solely utilized by the metabolism of the infectious organism selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; and c) determining the location of the infectious organisms present in the host by detecting the labeled substrate in the body of the mammalian host.

In accordance with an embodiment, the present invention provides a method for detection of the presence of gram negative organisms in a mammalian host comprising: a) administering to the host a therapeutically effective amount of a labeled substrate comprising labeled sorbitol and/or derivatives thereof; b) allowing a sufficient period of time for the gram negative organisms to take up the labeled substrate; and c) determining whether the gram negative organisms are present in the host by detecting the labeled substrate in the body of the mammalian host.

In accordance with an embodiment, the present invention provides a method for detection of the presence of gram negative organisms in a mammalian host comprising: a) administering to the host a therapeutically effective amount of a labeled substrate comprising $^{18}$F-fluorodeoxysorbitol (FDS) and/or derivatives thereof; b) allowing a sufficient period of time for the gram negative organisms to take up the labeled substrate; and c) determining whether the gram negative organisms are present in the host by detecting the labeled substrate in the body of the mammalian host.

In accordance with another embodiment, the present invention provides a method for the determination of the efficacy of an antibiotic therapy in a mammalian host with a gram negative infection comprising: a) administering to the host a therapeutically effective amount of a labeled substrate comprising $^{18}$F-fluorodeoxysorbitol ([$^{18}$F]FDS) and/or derivatives thereof; b) allowing a sufficient period of time for the gram negative organism to take up the labeled substrate; c) determining the amount gram negative organisms are present in the host by detecting the labeled substrate in the body of the mammalian host; d) subjecting the mammalian host to antibiotic treatment for a selected period of time; e) repeating steps a)-c) one or more times; f) assessing whether the gram negative infection has been reduced after d) by comparing the amount of labeled substrate present before d) to the amount of labeled substrate present after d), wherein when the amount of labeled substrate present after d) is less, than a determination is made that the antibiotic treatment of d) is effective.

In accordance with a further embodiment, the present invention provides a method for the determination of the efficacy of an antibiotic therapy in a mammalian host with an infection comprising: a) administering to the host a therapeutically effective amount of a compound comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; c) determining the amount infectious organisms are present in the host by detecting the labeled substrate in the body of the mammalian host; d) subjecting the mammalian host to antibiotic treatment for a selected period of time; e) repeating steps a)-c) one or more times; f) assessing whether the infection has been reduced after d) by comparing the amount of labeled substrate present before d) to the amount of labeled substrate present after d), wherein when the amount of labeled substrate present after d) is less, than a determination is made that the antibiotic treatment of d) is effective.

In accordance with yet another embodiment, the present invention provides a method for identification of infectious prokaryotic organisms in a mammalian host comprising: a) administering to the host a therapeutically effective amount of two or more different compounds comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; and c) determining the identity of infectious prokaryotic organisms present in the host by detecting and quantifying the amount of each of the labeled substrates in the body of the mammalian host and comparing the quantities of each labeled substrate to a control for the specific species of prokaryotic organisms.

In accordance with an embodiment, the present invention provides a method for the determination of the appropriate an antibiotic therapy in a mammalian host with an infection comprising: a) administering to the host a therapeutically effective amount of two or more different compounds comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; c) determining the identity of infectious prokaryotic organisms present in the host by detecting and quantifying the amount of each of the labeled substrates in the body of the mammalian host and comparing the quantities of each labeled substrate to a control for the specific species of prokaryotic organisms; and d) selecting the appropriate antibiotic therapy after identification of the specific species of prokaryotic organisms present in the mammalian host.

BRIEF DESCRIPTION OF THE DRAWINGS

FIG. 2 is a table showing some of the compounds useful in the methods of the present invention.

FIG. 3 is a table showing the results of uptake assays of labeled substrates p-aminobenzoic acid (PABA), mannitol (MAN), 2,6-diaminopimelic acid (DAP), xylose (XYL), alpha-methyl-glucopyranoside (MGP), shikimic acid (SHIK), and cellobiose (CB) following incubation for 2 hours with exponentially growing *S. aureus, E. coli*, or *M. smegmatis*.

DETAILED DESCRIPTION OF THE INVENTION

Figure 1:
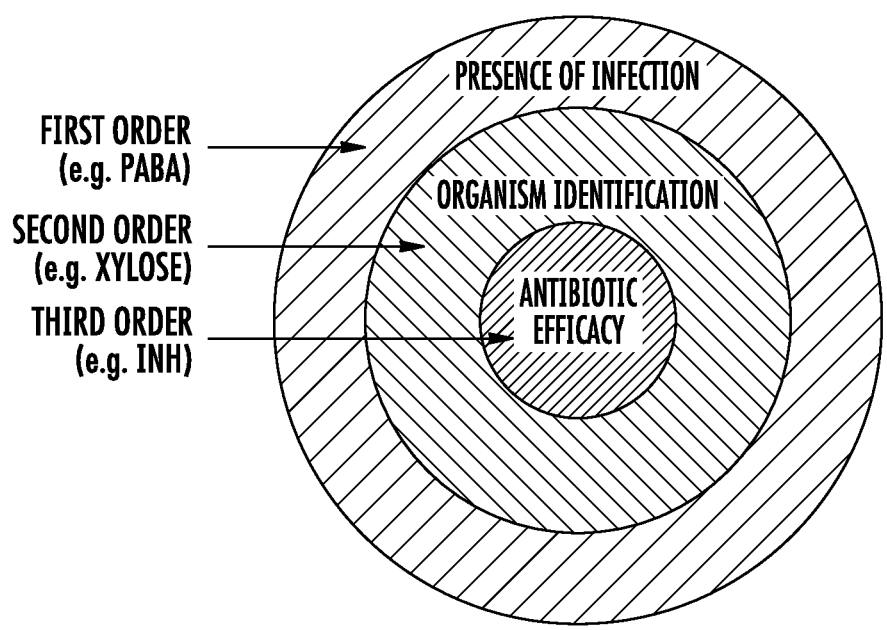
FIG. 1 illustrates some of the goals of infectious organism specific imaging methods of the present invention.

The methods of the present invention introduce an approach that has yielded a number of candidate molecular probes of infectious organisms, such as bacterial organisms, that are suitable for use as labeled substrates, such as radiolabeled, or dye labeled tracers. Previously proposed tracers, such as FIAU, require the presence of bacterial thymidine kinase, which is not present in some species of bacteria, such as *Mycobacterium tuberculosis*. The enzyme for folic acid synthesis from PABA, dihydropteroate synthase is widely expressed among species of bacteria, and moreover is synthesized in many other pathogens, such as *Pneumocystis jiroveci*, toxoplasma *gondii* and *Plasmodium* species.

In accordance with one or more embodiments of the present invention, the methods presented herein exploit unique biochemical pathways present within infectious organisms to develop a series of small molecule metabolic tracers that have the potential to diagnose and monitor the presence of infection (first order; differentiate infection from inflammation or other processes such as malignancies), organism identification (second order) and antimicrobial susceptibility (third order; information on antibiotic efficacy).

Therefore, in accordance with one or more embodiments of the present invention, labeled substrates including, for example, p-aminobenzoic acid (PABA), D-xylose (XYL), 2,6-diaminopimellic acid (DAP), methyl-alpha-D-glucopyranoside (MGP), shikimate (SHIK), cellobiose (CB) mannitol (MAN), and sorbitol (SOR) are useful for detection of a constellation of infectious diseases. Other embodiments include, but are not limited to sugars such as mannitol or sorbitol or derivatives thereof, and embodiments other sugars such or labeled substrates outlined above.

As used herein, the term "substrate" means any refers to a compound or protein or peptide or other biologically active molecule which is metabolized or otherwise taken up by a specific target infectious organism, such as, for example, a bacteria, but is not utilized in any significant amount, in the cellular metabolism of a mammalian host.

Examples of such compounds include compounds metabolized by prokaryote-specific pathways, 2) evidence for prokaryote accumulation or antimicrobial activity, and 3) absence of known eukaryotic accumulation or metabolism of these compounds.

As used herein, the term "labeled" means a compound or protein or peptide or other biologically active molecule which has a detectable moiety linked to it either covalently or via a linking molecule.

By "detectable label(s) or moieties" is meant a composition that when linked to a molecule of interest renders the latter detectable, via spectroscopic, photochemical, biochemical, immunochemical, chemical means or other imaging means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. Specific radioactive labels include most common commercially available isotopes including, for example, $^{3}$H, $^{11}$C, $^{13}$C, $^{15}$N , $^{18}$F, $^{19}$F, $^{123}$I, $^{124}$I, $^{125}$I, $^{131}$I, $^{86}$Y, $^{89}$Zr, $^{111}$In, $^{94m}$Tc, $^{99m}$Tc, $^{64}$Cu and $^{68}$Ga. Suitable dyes include any commercially available dyes such as, for example, 5(6)-carboxyfluorescein, IRDYE 680RD maleimide or IRDYE 800CW, ruthenium polypyridyl dyes, and the like. Also included in the labeled substrates of the present invention are substrates labeled with PET, SPECT or MRI detectable imaging agents or moieties.

In accordance with an embodiment, the labeled substrates of the present invention include $^{18}$F labeled substrates. Examples of such substrates include, but are not limited to, 2-fluoro-PABA, 3-fluoro-PABA, and 2-fluoro-mannitol. Other fluorinated substrates identified here are also within the scope of the present invention.

As used herein, the term "contacting" refers to any suitable method of bringing a labeled substrate suitable for imaging into contact with an infectious organism, e.g., bacteria, fungi, protozoa and virally infected cells of the host mammal. The term "contacting" can also refer to bringing a labeled substrate suitable for imaging into contact with an infectious organism, e.g., bacteria, fungi, protozoa and virally infected cells in vitro.

One of ordinary skill in the art would understand that use of the term "solely utilized by the metabolism of the infection organism" is meant to convey the concept that the labeled substrate is a significant substrate in one or more metabolic pathways of the infectious organism, while it has little or no significant use as a substrate in the metabolic activity of normal cells in the mammalian host.

In accordance with an embodiment, the present invention provides a method for detection of the presence of infectious organisms in a mammalian host comprising: a) administering to the host a therapeutically effective amount of a compound comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; and c) determining whether the infectious organisms are present in the host by detecting the labeled substrate in the body of the mammalian host.

As used herein, the term "infectious organisms" includes microbiological organisms that can infect the host mammal. Prokaryotic organisms, such as bacteria, both gram positive and gram negative bacteria are included. One of ordinary skill would understand that in the context of the methods of the present invention, the definition also is inclusive of other microbiological organisms which can infect a mammalian host and which have at least one or more metabolic processes or enzymes that are not found in any significant amounts in the mammalian host, which can be the target of the labeled substrates of the present invention. As such, organisms such as fungi, protozoa, parasites and also mammalian cells which have been infected by certain viruses.

In accordance with an embodiment, the detectable moiety is a fluorescent dye. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarine, rhodamine, xanthene, fluorescein, boron~dipyrromethane (BODIPY), Cy5, Cy5.5, Cy7, VIVOTAG-680, VIVOTAG-S680, VIVOTAG-S750, ALEXAFLUOR660, ALEXAFLUOR680, ALEXAFLUOR700, ALEXAFLUOR750, ALEXAFLUOR790, DY677, DY676, DY682, DY752, DY780, DYLIGHT547, DYLIGHT647, HILYTE FLUOR 647, HILYTE FLUOR 680, HILYTE FLUOR 750, IRDYE 800CW IRDYE 800RS, IRDYE 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (borondipyrromethane) dyes have a general structure of 4,4'-difluoro-4-bora-3a, 4a-diaza-s-indacene) and sharp fluorescence with high quantum yield and excellent thermal and photochemical stability.

Other imaging agents which can be used in the labeled substrates of the present invention include PET and SPECT imaging agents. The most widely used agents include branched chelating agents such as di-ethylene tri-amine penta-acetic acid (DTPA), 1,4,7,10-tetra-azacyclododecane-1,4,7,10-tetraacetic acid (DOTA) and their analogs. Chelating agents, such as di-amine dithiols, activated mercaptoacetyl-glycyl-glycyl-glycine (MAG3), and hydrazidonicotinamide (HYNIC), are able to chelate metals like $^{99m}$Tc and $^{186}$Re. Instead of using chelating agents, a prosthetic group such as N-succinimidyl-4-$^{18}$F-fluorobenzoate ($^{18}$F-SFB) is necessary for labeling peptides with $^{18}$F.

In accordance with another embodiment, the present invention provides a labeled substrate, wherein the label is covalently linked to the substrate and the label comprises a compound or enzyme that produces light or a photon, which is detectable when in the presence of a substrate in the target microorganism. An example of such a substrate is luciferase, where in the presence of ATP within the organism, luciferase will react with ATP and produce a photon. One of ordinary skill in the art will understand that there are other enzyme and reporter complexes which can be used in the art.

In accordance with an embodiment, the detectable moiety may be attached to the substrate by a linker molecule. For instance linking groups having alkyl, aryl, combination of alkyl and aryl, or alkyl and aryl groups having heteroatoms may be present. For example, the linker can be a $C_1$-$C_{20}$ alkyl, $C_2$-$C_{20}$ alkenyl, $C_2$-$C_{20}$ alkynyl, $C_1$-$C_{20}$ hydroxyalkyl, $C_1$-$C_{20}$ alkoxy, $C_1$-$C_{20}$ alkoxy $C_1$-$C_{20}$ alkyl, $C_1$-$C_{20}$ alkylamino, di-$C_1$-$C_{20}$ alkylamino, $C_1$-$C_{20}$ dialkylamino $C_1$-$C_{20}$ alkyl, $C_1$-$C_{20}$ thioalkyl, $C_2$-$C_{20}$ thioalkenyl, $C_2$-$C_{20}$ thioalkynyl, $C_6$-$C_{22}$ aryloxy, $C_6$-$C_{22}$ arylamino $C_2$-$C_{20}$ acyloxy, $C_2$-$C_{20}$ thioacyl, $C_1$-$C_{20}$ amido, and $C_1$-$C_{20}$ sulphonamido.

As used herein, the term "therapeutically effective amount" means that the one or more labeled substrates are administered to a subject in vivo in an amount that is sufficient to effectively target the infectious organisms of interest and which can be detected in the subject over a reasonable time frame. In other embodiments, the term "therapeutically effective amount" means that the one or more labeled substrates are placed in contact with the infectious organisms of interest in vitro and which can be detected in the organisms over a reasonable time frame.

In accordance with an embodiment, the present invention provides a pharmaceutical composition comprising one or more labeled substrates described herein and a pharmaceutically acceptable carrier.

In another embodiment, the present invention provides a pharmaceutical composition comprising one or more labeled substrates described herein, a pharmaceutically active compound, and a pharmaceutically acceptable carrier.

In accordance with an embodiment, the present invention provides a use of the labeled substrates described herein, in an effective amount, to prepare a medicament, preferably for use as a medicament for treating a disease in a subject.

In accordance with an embodiment, the present invention provides a pharmaceutical composition comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; wherein the composition includes a pharmaceutically and physiologically acceptable carrier, in an amount effective for use in a medicament, and most preferably for use as a medicament for use in the detection of the presence of infectious organisms in a mammalian host, wherein the pharmaceutical composition is administered to the host, and after allowing a sufficient period of time for the infectious organism to take up the labeled substrate, a determination is made whether the infectious organisms are present in the host by detecting the labeled substrate in the body of the mammalian host.

In accordance with another embodiment, the present invention provides a pharmaceutical composition comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; wherein the composition includes a pharmaceutically and physiologically acceptable carrier, in an amount effective for use in a medicament, and most preferably for use as a medicament for detection of the location of infectious organisms in the body of a mammalian host, wherein the pharmaceutical composition is administered to the host, and after allowing a sufficient period of time for the infectious organism to take up the labeled substrate, the location of the infectious organisms present in the host is determined by detecting the labeled substrate in the body of the mammalian host.

In accordance with a further embodiment, the present invention provides a pharmaceutical composition comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; wherein the composition includes a pharmaceutically and physiologically acceptable carrier, in an amount effective for use in a medicament, and most preferably for use as a medicament for determination of the efficacy of an antibiotic therapy in a mammalian host with an infection, wherein the pharmaceutical composition is administered to the host, and after allowing a sufficient period of time for the infectious organism to take up the labeled substrate, the amount infectious organisms present in the host are determined by detecting the labeled substrate in the body of the mammalian host, followed by subjecting the mammalian host to antibiotic treatment for a selected period of time; repeating the administration of the pharmaceutical composition and after allowing a sufficient period of time for the infectious organism to take up the labeled substrate, the amount infectious organisms present in the host are again determined by detecting the labeled substrate in the body of the mammalian host; and assessing whether the infection has been reduced after treatment with the antibiotic by comparing the amount of labeled substrate present before treatment to the amount of labeled substrate present after treatment, wherein when the amount of labeled substrate present after treatment is less, a determination is made that the antibiotic treatment of is effective.

In accordance with an embodiment, the present invention provides a pharmaceutical composition comprising a labeled substrate, wherein the substrate is $^{18}$F-fluorodeoxysorbitol ([$^{18}$F]FDS) and/or derivatives thereof; wherein the composition includes a pharmaceutically and physiologically acceptable carrier, in an amount effective for use in a medicament, and most preferably for use as a medicament for use in the detection of the presence of gram negative organisms in a mammalian host, wherein the pharmaceutical composition is administered to the host, and after allowing a sufficient period of time for the gram negative organism to take up the labeled substrate, a determination is made whether the gram negative organisms are present in the host by detecting the labeled substrate in the body of the mammalian host.

In some other embodiments, the medicament further comprises a pharmaceutically acceptable carrier.

In a further embodiment, the medicament further comprises a second therapeutic agent. In some embodiments, the therapeutic agent is an anti-infective agent, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives.

A therapeutic agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

In accordance with an embodiment of the present invention, the amount of time of exposure of the labeled substrates to the infectious organisms in the subject should be sufficiently long to effect uptake of the labeled substrate in the infectious organisms in the subject. The time for the desired effect varies with dosage, target, age and other factors known to those of skill in the art. Generally, the time of exposure of the labeled substrates to the infectious organisms should range from about 1 hour to about 120 hours, preferably from about 1 hour to about 24 hours, more preferably from about 1 hour to about 12 hours.

With respect to labeled substrates described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular labeled substrate, as well as by the particular method used to administer the composition. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the labeled substrates of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications. A particular example of a pharmaceutically active compound is an antibiotic agent.

The term "antibiotic agent" as well as words stemming therefrom, as used herein, generally includes pharmaceutically or therapeutically active compounds that work by interfering with the metabolism of the infectious organism. Antibacterial antibiotics are commonly classified based on their mechanism of action, chemical structure, or spectrum of activity. Most target bacterial functions or growth processes. Those that target the bacterial cell wall (penicillins and cephalosporins) or the cell membrane (polymixins), or interfere with essential bacterial enzymes (quinolones and sulfonamides) have bactericidal activities. Those that target protein synthesis (aminoglycosides, macrolides, and tetracyclines) are usually bacteriostatic. Further categorization is based on their target specificity. "Narrow-spectrum" antibacterial antibiotics target specific types of bacteria, such as gram-negative or gram-positive bacteria, whereas broad-spectrum antibiotics affect a wide range of bacteria.

In accordance with an embodiment, the antibiotic agents used in the methods of the present invention may include other drugs effective against fungi, protozoans and antivirals.

For purposes of the invention, the amount or dose of the labeled substrates of the present invention that is administered should be sufficient to effectively target the infectious organisms in vivo, such that the uptake of the labeled substrates can be detected, in the subject over a reasonable time frame. The dose will be determined by the efficacy of the particular labeled substrate formulation and the location of the infectious organisms in the subject, as well as the body weight of the subject to be treated.

The dose of the labeled substrates of the present invention also will be determined by the existence, nature and extent of any adverse side effects that might accompany the administration of a particular labeled substrate. Typically, an attending physician will decide the dosage of the labeled substrates with which to treat each individual subject, taking into consideration a variety of factors, such as age, body weight, general health, diet, sex, compound to be administered, route of administration, and the severity of the condition being treated. By way of example, and not intending to limit the invention, the dose of the labeled substrates of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the labeled substrates of the present invention can be at a concentration from about 1 nM to about 10,000 nM, preferably from about 10 nM to about 5,000 nM, more preferably from about 100 nM to about 500 nM.

In another embodiment, the term "administering" means that at least one or more labeled substrates of the present invention are introduced into a subject, preferably a subject receiving treatment for a disease, and the at least one or more labeled substrates are allowed to come in contact with the one or more disease related infectious organisms in vivo.

As used herein, the term "treat," as well as words stemming therefrom, includes diagnostic and preventative as well as disorder remitative treatment.

As used herein, the term "mammalian host" or "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In a further embodiment, the labeled substrates of the present invention can be used in combination with one or more additional therapeutically active agents which are known to be capable of treating conditions or diseases discussed above. For example, the described labeled substrates of the present invention could be used in combination with one or more known therapeutically active agents, to treat a disease or condition.

As used herein, the term "detection" "imaging" or "radiodetection" means the use of certain properties of isotopes and the energetic particles emitted from radioactive material to diagnose or treat various medical conditions. In addition, the term "scintigraphy" means a diagnostic test in which a two-dimensional image of a body having a radiation source is obtained through the use of radioisotopes. A radioactive chemical is injected intravenously into the patient which then concentrates in the target cells or organ of interest. By placing a camera that senses radioactivity over the body, an image of the target cells or organ of interest can be created. The particles can be detected by suitable devices such as gamma cameras, positron emission tomography (PET) machines, single photon emission computed tomography (SPECT) machines and the like.

In accordance with some embodiments, the term "imaging" or "detection" can also include detection of photons as from a fluorescent dye on the labeled substrate.

In accordance with another embodiment, the present invention provides a method for detection of the location of infectious organisms in the body of a mammalian host comprising: a) administering to the host a therapeutically effective amount of a compound comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; and c) determining the location of the infectious organisms present in the host by detecting the labeled substrate in the body of the mammalian host.

In accordance with an embodiment, the present invention provides a method of diagnosing, locating, and assessing the efficacy of treatment of an infectious disease in a patient comprising administering to a subject suspected of having said disease, a labeled substrate prepared according to the above methods, which is selectively taken up by an infectious organism, obtaining a diagnostic image of the subject, determining the location of labeled substrate taken up by the infectious organisms in the subject, and correlating the location of the sequestered labeled substrate with the location of the infectious organisms in the subject. When the detectable moiety is a positron emitter, such as $^{18}F$, the spectroscopy can be, for example, SPECT, PET, gamma scintigraphy, or MRI.

In accordance with a further embodiment, the present invention provides a method for the determination of the efficacy of an antibiotic therapy in a mammalian host with an infection comprising: a) administering to the host a therapeutically effective amount of a compound comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; c) determining the amount infectious organisms are present in the host by detecting the labeled substrate in the body of the mammalian host; d) subjecting the mammalian host to antibiotic treatment for a selected period of time; e) repeating steps a)-c) one or more times; f) assessing whether the infection has been reduced after d) by comparing the amount of labeled substrate present before d) to the amount of labeled substrate present after d), wherein when the amount of labeled substrate present after d) is less, than a determination is made that the antibiotic treatment of d) is effective.

As used herein, the term "identification" with respect to the inventive methods means that certain species of infectious organisms will preferentially uptake specific labeled substrates while not taking up other labeled substrates, thus allowing one of ordinary skill in the art to deduce the genus and/or species of infectious organism when administering to a subject at least two different labeled substrates. In accordance with one or more embodiment, three, four, five or more different labeled substrates can be administered to a subject and the amount of uptake, based on radiodetection, or fluorescence or another signal, will allow one of skill to make a determination of the species of infections organism infecting the subject.

In accordance with another embodiment of the present invention, labeled D-xylose, in contrast, represents the first molecular probe with the capacity to differentiate between gram negative and gram positive bacteria, with selective uptake only into the latter.

In accordance with yet another embodiment, the present invention provides a method for identification of infectious prokaryotic organisms in a mammalian host comprising: a) administering to the host a therapeutically effective amount of two or more different compounds comprising a labeled substrate, wherein the substrate is a compound that is solely utilized by the metabolism of the infectious organisms selected from the group consisting of prokaryotes, fungi, protozoa, and virally infected host cells; and wherein the label of the labeled substrate is a detectable moiety selected from the group consisting of radionuclides, near-infrared dyes, and fluorescent dyes; b) allowing a sufficient period of time for the infectious organism to take up the labeled substrate; and c) determining the identity of infectious prokaryotic organisms present in the host by detecting and quantifying the amount of each of the labeled substrates in the body of the mammalian host and comparing the quantities of each labeled substrate to a control for the specific species of prokaryotic organisms.

The Enterobacteriaceae is a family of rod-shaped gram-negative bacteria that normally inhabit the gastrointestinal tract and is a frequent source of community and hospital acquired infections. Notable examples include pathogens such as *Escherichia coli, Yersinia pestis, Klebsiella pneumoniae* and *Enterobacter* species producing illnesses ranging from pneumonia, meningitis, sepsis, peritonitis, pyelonephritis, etc. Patient mortality approaches 50% in cases of sepsis associated with carbapenem-resistant enterobacteriaceae (CRE). When the source of infection is not clear, noninvasive diagnostic tools are needed to spatially localize and quantify bacteria. The source of infection may thereby be identified and the success of an intervention monitored. 2-[$^{18}$F]-Fluorodeoxyglucose ([$^{18}$F]FDG) positron emission tomography (PET) has emerged as a sensitive, noninvasive approach to detect metabolically active oncologic, rheumatic or infectious processes, but cannot reliably differentiate one process from the other. In accordance with one or more embodiments, the present inventors have developed 2-[$^{18}$F]-fluorodeoxysorbitol ([$^{18}$F]FDS) as a specific imaging probe for infection by gram negative enterobacteria. Sorbitol is a sugar alcohol approved by the Food and Drug Administration (FDA) as a surgical irrigant and "sugar free" sweetener, yet is metabolized by prokaryotic-specific pathways on selective media. In the examples disclosed herein, commercially available [$^{18}$F]FDG was rapidly (<30 minutes) converted into [$^{18}$F]FDS, and which then specifically visualized *E. coli* myositis and *K. pneumoniae* pulmonary infection by PET. The technology of the present invention is readily translatable from animal models to humans for clinical use including patients undergoing anticancer treatment with bacterial infections due to Enterobacteriaceae.

In accordance with an embodiment, the present invention provides a specific gram negative prokaryotic organism substrate which is useful in the differentiation of gram positive from gram negative infection in a host. As shown herein, the $^{18}$F labeled SOR substrate fluorodeoxysorbitol (([$^{18}$F]FDS) and derivatives thereof, is actively taken up by gram negative organisms and not taken up by gram positive organisms. Labeling sorbitol with $^{18}$F (to produce ([$^{18}$F]FDS) can be utilized as a means of differentiating gram negative infection from gram positive infection in addition to localizing and quantifying infectious disease burden. This substrate would therefore have an impact on the clinical decision to begin empiric antibiotic therapy as well as the choice of antibacterial agents. In another embodiment, SOR could be labeled with $^{11}$C.

[$^{18}$F]FDS represents the first radio-probe specific for Enterobacteriaceae. Clinically, the probe has numerous applications since the selection of antibiotics is roughly divided by activity against gram positive and negative organisms. Treatment is given empirically while diagnostic tests are performed. This process is invasive, labor intensive, time consuming, and subject to incorrect sampling and contamination. Rapid source control and pathogen identification can guide antibiotic choice and limit drug toxicity. Repeat imaging can monitor treatment efficacy, or suggest the presence of a drug resistant infection, of which the Enterobacteriaceae are notorious.

Carbapenem-resistant Enterobacteriaceae is a serious public health threat which has spread from hospital to community settings. Because CRE are resistant to many classes of antibiotics, achieving source control is essential to successful therapy. Noninvasive, whole host imaging provides an important tool to localize and monitor infection. Even the timely administration of antibiotics with in vitro activity against carbapenem-resistant *K. pneumoniae* was not associated with patient survival. Removal of the focus of infection (i.e., debridement) was independently associated with patient survival (P=0.002).

The minimal background signal makes the probes of the present invention attractive candidates for visualizing infection in privileged, difficult to sample compartments, such as the brain. The high signal to noise ratio is particularly promising at the high bacterial burden tested, but future studies will aim to decrease the limit of bacilli detected. Since [$^{18}$F]FDG-PET imaging is widely available, [$^{18}$F] FDS-PET is readily translatable from animal models to humans for clinical use.

EXAMPLES

The chemicals used in the study were all purchased from commercial vendors and were used without further purification except where stated. 2-[$^{18}$F]-Fluorodeoxyglucose was purchased from PETNET Solutions Inc. (Philadelphia, Pa.). Chemical and radiochemical purities were determined by an analytical HPLC system equipped with a Phenomenex Rezex RCM-Monosaccharide Ca$^{++}$ (8%) Column and both UV and radioactivity detectors. Structure was confirmed by $^{1}$H, $^{13}$C NMR and mass spectrometry. Sorbitol concentration was measured by a commercial colormetric assay (BioVision, Milpitas, Calif.).

In vitro uptake assays: Freeze dried reference strains of various bacterial species were purchased from American Type Culture Collection (Manassas, Va.) and grown to mid-log phase (OD$_{600}$ 1.0) in Lysogeny Broth (LB) or Middlebrook 7H9 broth supplemented with 10% oleic acid-albumin-dextrose-catalase (Difco, Detroit, Mich.) and 0.05% Tween 80 (Sigma). The number of colony forming units (CFUs) were enumerated by dilution and plating onto solidified media. Tracer uptake assays were performed by incubating bacterial cultures with 7.4 kBq per ml culture of tracer at 37° C. with rapid agitation for 4 hours, with sampling at 0, 30, 120, and 240 minutes. As a control, heat killed (90° C. for 20 minutes) bacteria were similarly incubated with each tracer. Bacteria were pelleted by centrifugation and washed three times with PBS. The activity for each pellet was measured using an automated gamma counter (1282 Compugamma CS Universal gamma counter, LKB Wallac). Background counts were subtracted from sample counts. Six independent replicates were used for each tracer, and for each bacterial strain. Uptake was expressed as the percentage of total tracer added to the culture that resided within the cell pellet.

A commercial library of over 400 random $^{14}$C and $^{3}$H radio-labeled small molecules (metabolites for nucleic acids, amino acids, lipid synthesis, antibiotics, cofactors, etc) were screened from Moravek Biochemicals, Inc. (Brea, Calif.). Each compound was scored by the following selection criteria: 1) metabolized by prokaryote specific pathways, 2) evidence for prokaryote accumulation or antimicrobial activity, and 3) absence of known eukaryotic accumulation or metabolism. A score +1 or −1 for passing or failing (0 if information unavailable), was assigned to each molecule and for each selection criteria.

In vivo infection. 5-6 week female CBA/J mice (n=3 per group) were immunosuppressed with cyclophosphamide as described by Zuluaga et al. (BMC Infect Dis, 2006. 6: p. 55), then injected with 1×10$^{7}$ *E. coli* in the right thigh and either 50 µg LPS, heat inactivated *E. coli*, or live *S. aureus* in the left thigh. For heat inactivation, the live culture was placed on wet ice and an aliquot was subjected to a 90° C. water bath for 20 minutes. For a pneumonia model, 3×10$^{6}$ *K. pneumoniae* were instilled into the mainstem bronchus of sedated, neutropenic mice as described by Rouse et al (Animal Models of Gram-negative Bacillary Experimental Pneumonia, in Handbook of animal models of infection, O. Zak and M. A. Sande, Editors. 1999, Academic Press: London, UK. p. 495-500). The night before each imaging time-point, mice were fasted for 12 hours. Water was provided ad libitum. 7.4 MBq [$^{18}$F]FDS was injected by tail vein 2 hours prior to collecting a static 15 minute frame injection using a MOSAIC HP (Philips) Small Animal PET. [$^{18}$F]FDG was injected 45 minutes prior to data collection as described by Davis et al (Antimicrob Agents Chemother, 2009. 53(11): p. 4879-84). CT scans were performed at the same time with a NANOSPECT/CT (BIOSCAN) in vivo animal imager. PET data were reconstructed and co-registered with CT images. Mice were sacrificed to collect tissues for direct gamma counting and to determine the number of bacilli implanted. The thighs were homogenized in PBS and plated onto solidified LB media overnight at 37° C. to enumerate the colony forming units (CFU). At least 3 mice were used for each group.

Figure 5:
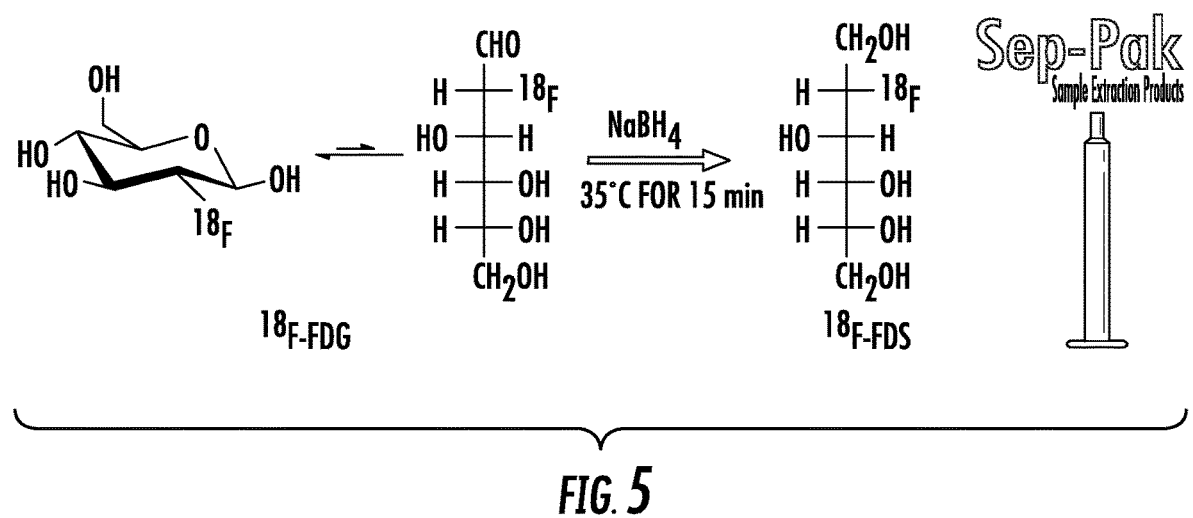
FIG. 5 is an illustration of 2-[$^{18}$F]-fluorodeoxyglucose and its conversion to 2-[$^{18}$F]-fluorodeoxysorbitol using the methods disclosed herein.

Synthesis of $^{18}$F-fluorodeoxysorbitol ([$^{18}$F]FDS). The novel gram-negative bacteria-specific imaging biomarker [$^{18}$F]FDS can be synthesized rapidly and easily at very low cost using the most commonly used PET tracer $^{18}$F-fluorodeoxyglucose, which is commercially available all over the world. Previously proposed tracers either require complex chemical synthesis or utilize expensive radioisotopes (e.g. I-124 in FIAU) which could limit their widespread use. However, [$^{18}$F]FDS can be rapidly (<30 min) synthesized from [$^{18}$F]FDG using a low cost technique (Li Z B, et al., Mol. Imaging Biol., 2008; 10:92-8) and is shown in FIG. 5. Briefly, we used the method of Li et al to generate [$^{18}$F]FDS from commercially available 2-[$^{18}$F]-Fluorodeoxyglucose (PETNET Solutions Inc., Philadelphia, Pa.) by chemical reduction with sodium borohydride. The reaction proceeded at 35° C. for 30 minutes, then was quenched with ascetic acid and pH corrected to 7.5 with sodium bicarbonate. FDS structure was confirmed by NMR and mass spectrometry Moreover, we have discovered that SOR, and its labeled derivative, [$^{18}$F]FDS is taken up specifically by gram-negative but not gram-positive bacteria and can be used to imaging infections in vivo (mouse model). Collectively, these data suggest that we have been able to develop a low-cost gram-negative bacteria-specific imaging biomarkers that can be manufactured easily at almost all PET centers in the world.

[$^{18}$F]FDS uptake and imaging. In vitro uptake assays exposed bacterial cultures to 7.4 kBq per ml [$^{18}$F]FDS over 2 hours, then cells were pelleted, washed and gamma counted. Intracellular uptake assays were performed at least in triplicate and indicate the percent of the total radioactivity (added to the culture), that was found in the bacterial pellet (after several steps of washing). Heat-killed bacteria were used as negative controls and no uptake was noted in any species. For in vivo studies, 5-6 week female CBA/J mice (n=3 per group) were immunosuppressed with cyclophosphamide then innoculated with bacteria as specified. 7.4 MBq [$^{18}$F]FDS or [$^{18}$F]FDG was injected by tail vein 2 hours prior to collecting a static 15 minute frame for myositis imaging. For pulmonary infection imaging, 18.5 MBq [$^{18}$F]FDS was injected, and images were collected by dynamic windows of 15 minutes over the course of 180 minutes. CT scans were performed for coregistration with PET images. Tissues were collected for direct gamma counting.

For semiquantitative analysis, 1-2 spherical (3 mm diameter) regions of interest (ROI) were drawn manually in the thighs using CT as a guide of each animal. The standard uptake values (SUV) were computed by normalizing the ROI activity for each mouse to the injected dose and animal weight using Amide version 0.9.1 (amide.sourceforge.net). For each group, the mean PET activity at each time-point was calculated by averaging the normalized thigh SUVs of all the ROIs in that group. Amira version 5.4.2 (amira.com) was used to visualize the images.

All protocols were approved by the Johns Hopkins Biosafety, Radiation Safety and Animal Care and Use Committees.

Statistical analysis. Statistical comparison between groups was performed using one tail distribution, two sample, unequal variance t-test in Excel 2007 (Microsoft). Data are presented on a linear scale as mean±standard error for the mean PET activities.

Example 1

Seven (3%) compounds (FIG. 2) passed all 3 selection criteria; of these 1 was a known substrate for TK similar to FIAU (which also validated the screen), while the remaining 6 compounds were novel and tested for intracellular bacterial accumulation in model bacteria representing three important pathogen classes: *Staphylococcus aureus* (gram-positive), *Escherichia coli* (gram negative), or *Mycobacterium smegmatis* (mycobacteria). Intracellular uptake assays were performed at least in triplicate and indicate the percent of the total radioactivity (added to the culture), that was found in the bacterial pellet (after several steps of washing) (FIG. 3). Heat-killed bacteria were used as negative controls and no uptake was noted in any species. Intriguingly, some compounds were taken up differentially by the 3 different species of bacteria (e.g. XYL for *E. coli* alone, DAP for *E. coli* and *M. smegmatis*) indicating that the present inventive imaging methods can identify other bacterial species. Sulfonamides are well known inhibitors of folate synthesis (PABA), beta-lactam antibiotics block peptidoglycan cross-link formation (DAP), and shikimate analogs (SHIK), such as 6-fluoro-shikimate have potent anti-bacterial activity in vitro.

Example 2

Figure 4A:
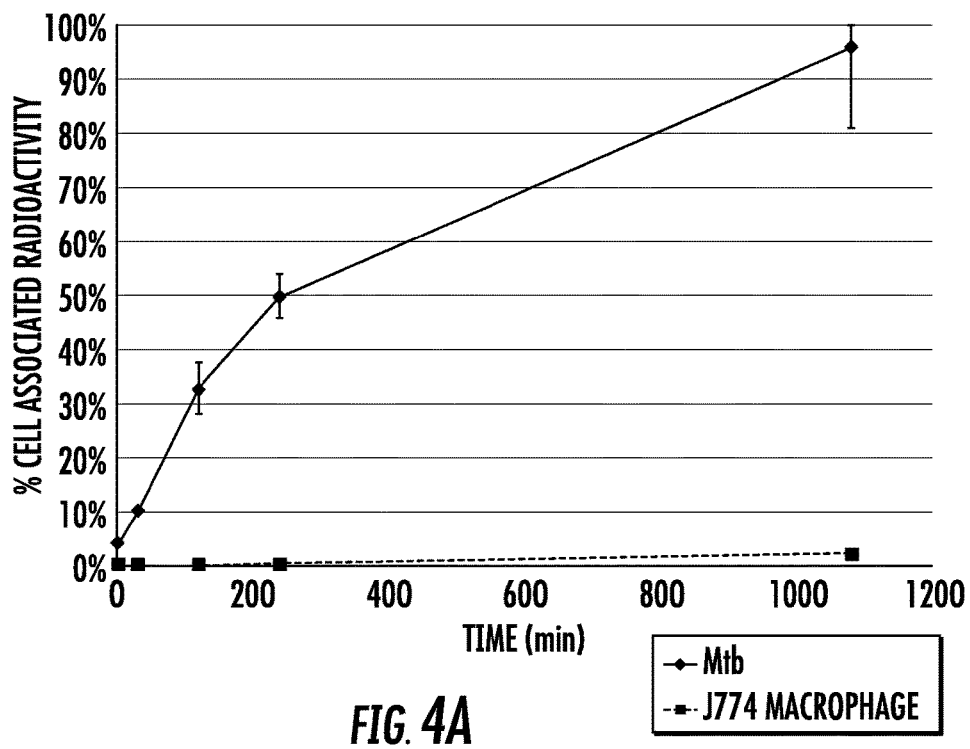
FIG. 4A is a graph showing significant and rapid accumulation of PABA (♦) is noted in *M. tb*. Note that there is no significant accumulation in host-cells (J774 macrophages) (■), indicating that the uptake is bacteria-specific.
Figure 4B:
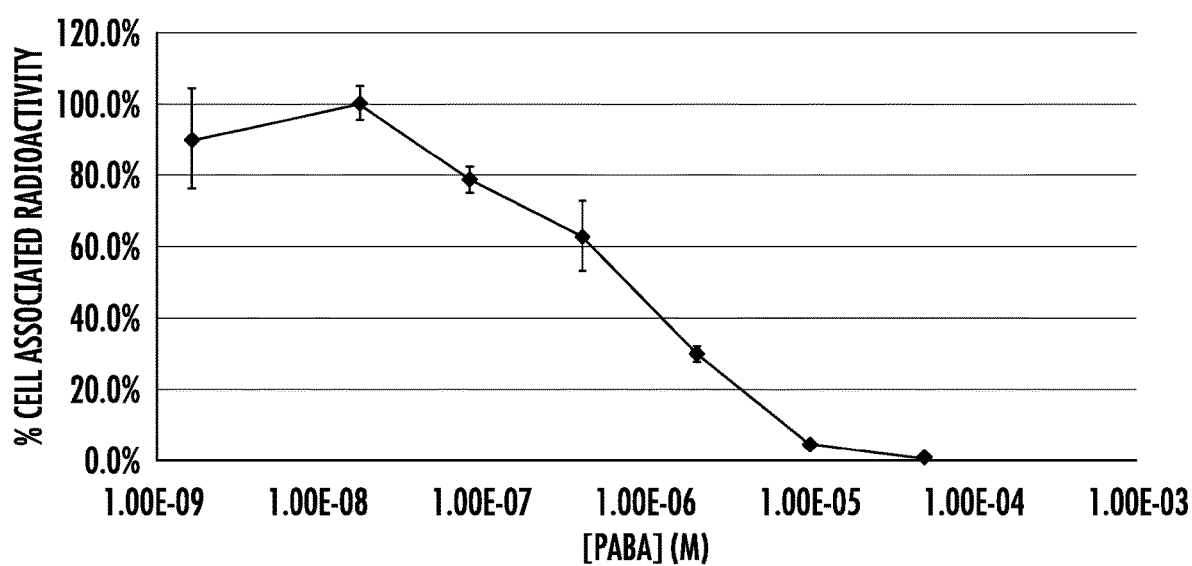
FIG. 4B is a graph showing PABA uptake in *M. tb*. is saturable and specific, as addition of excess unlabelled tracer blocks bacteria-associated activity.
Figure 4C:
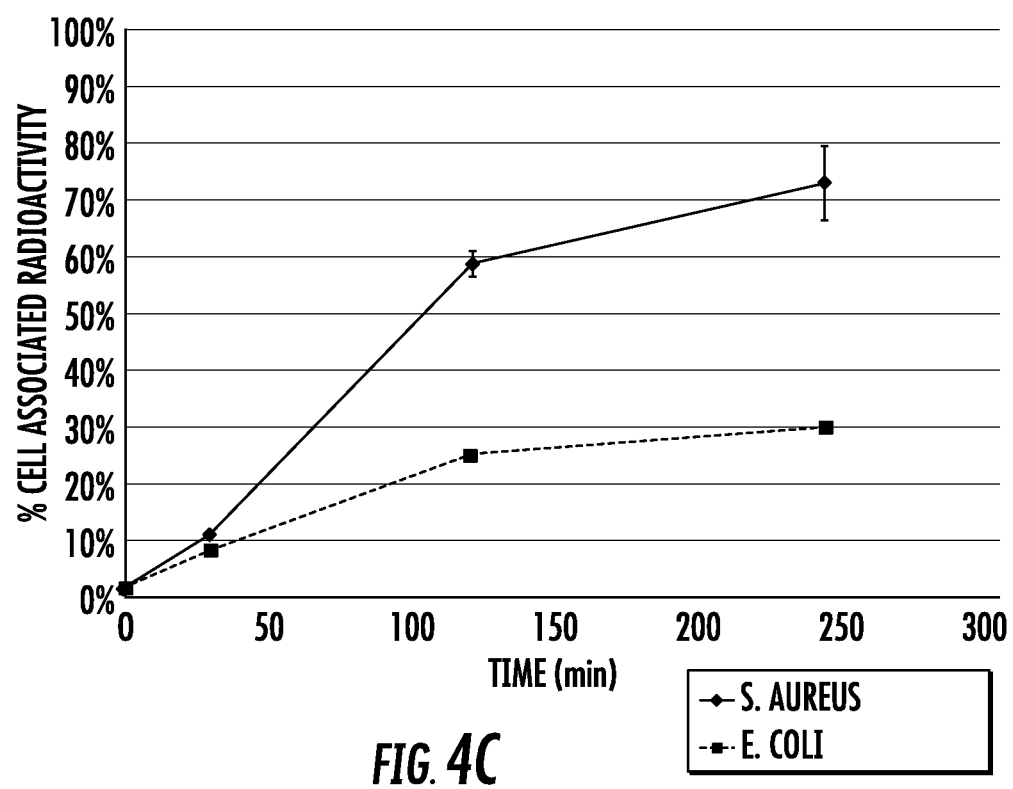
FIG. 4C is a graph showing PABA uptake in *S. aureus*, and *E. coli* in mid log cultures (1.0 O.D. 600). Heat-killed bacteria were used as controls for all assays (4A-4C) in which no uptake was noted in any species. Intracellular uptake assays were performed at least in triplicate and indicate the percent of the total radioactivity (added to the culture), that was found in the bacterial pellet (after several steps of washing).

A mycobacterial lead compound (PABA) was also evaluated in *Mycobacterium tuberculosis* and demonstrated significant (96.3% at 18-hours) and rapid (32.9% at 2-hours) accumulation. No significant accumulation was noted in host-cells (J774 macrophages) at the corresponding time-points, indicating that the uptake is bacteria-specific (FIG. 4A). Moreover, addition of excess unlabelled tracer blocked accumulation of *M. tuberculosis*-associated activity, indicating that PABA uptake was saturable and specific (FIG. 4B). PABA uptake was also measured in *S. aureus* and *E. coli* cultures and was also saturable and specific (FIG. 4C).

Example 3

[$^{14}$C] D-mannitol was another of the promising molecules identified by the methods of the present invention. It accumulated rapidly and in significant amounts in all three models bacteria tested. Intracellular uptake was 66%, 82% and 83% in *S. aureus, E. coli* and *M. smegmatis* respectively after only 2 hours of incubation (FIG. 3). No uptake was observed in heat killed bacteria. Moreover, uptake in macrophage-like cells (J774) and Human Brain Microvascular Endothelial Cells (HBMEC) was <5% uptake at 2 hours.

Example 4

Figure 6A:
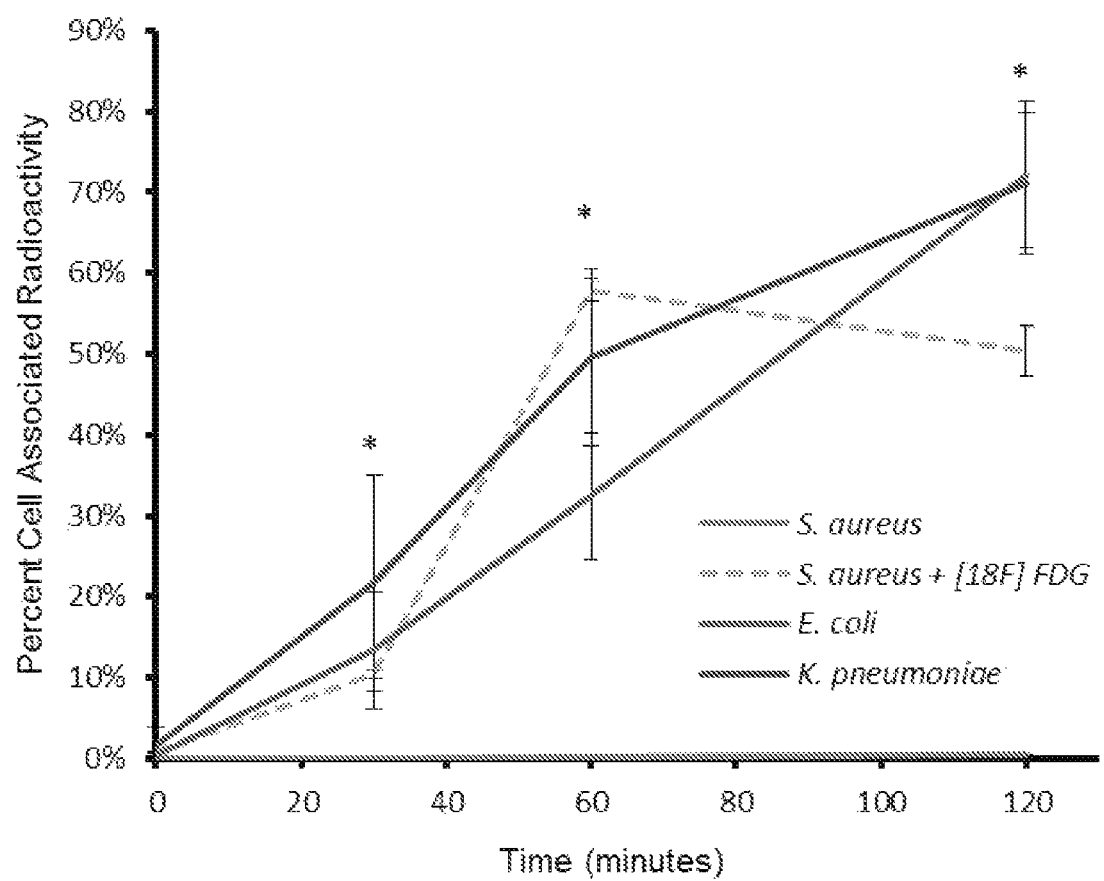
FIG. 6A is a graph showing that, the two gram-negative enteric species readily accumulated [$^{18}$F]FDS over time, with 72.2%±9.0% of the probe associated with *E. coli* and 71.1%±8.6% in *K. pneumoniae* after 120 minutes. *Staphylococcus aureus*, a gram positive control, did not significantly incorporate [$^{18}$F]FDS (0.47%±0.09%), but instead accumulated [$^{18}$F]FDG to 50.3%±3.1%.

Differentiation of microbes by selective growth media is a mainstay of clinical microbiology practice, such as MacConkey agar supplemented with sorbitol to isolate pathogenic *E. coli*. To identify infection in vivo, we extended this approach to selectively label Enterobacteriaceae with positron emitting fluorodeoxysorbitol. We efficiently converted commercially available [$^{18}$F]FDG to [$^{18}$F]FDS by chemical reduction in less than 30 minutes. We first tested cultures of *E. coli* K12 and *K. pneumoniae* to assess accumulation of the probe in vitro (FIG. 6A). As predicted, the two gram-negative enteric species readily accumulated [$^{18}$F]FDS over time, with 72.2%±9.0% of the probe associated with *E. coli* and 71.1%±8.6% in *K. pneumoniae* after 120 minutes. *Staphylococcus aureus*, a gram positive control, did not significantly incorporate [$^{18}$F]FDS (0.47%±0.09%), but instead accumulated [$^{18}$F]FDG to 50.3%±3.1%. Consistent with the selectivity of [$^{18}$F]FDS, eukaryotic J774 macrophage and WEHI 164 fibroblast cell lines only accumulated [$^{18}$F]FDG and not [$^{18}$F]FDS (data not shown). Likewise, heat killed organisms did not incorporate either probe (data not shown).

Figure 6B:
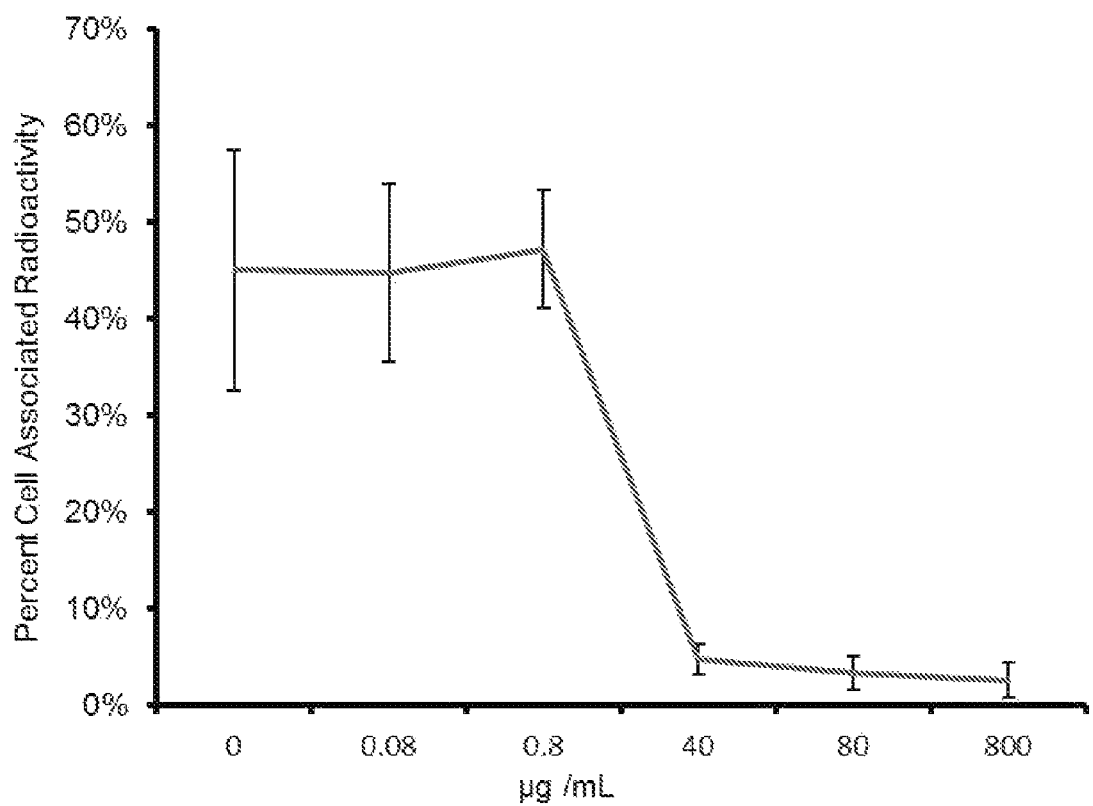
FIG. 6B is a graph showing that co-incubated *E. coli* cultures with [$^{18}$F]FDS and increasing concentrations of unlabeled sorbitol. [$^{18}$F]FDS uptake was outcompeted by concentrations of sorbitol above 40 μg/ml, indicating that the accumulation of [$^{18}$F]FDS was a saturable, presumably transporter driven process.
Figure 6C:
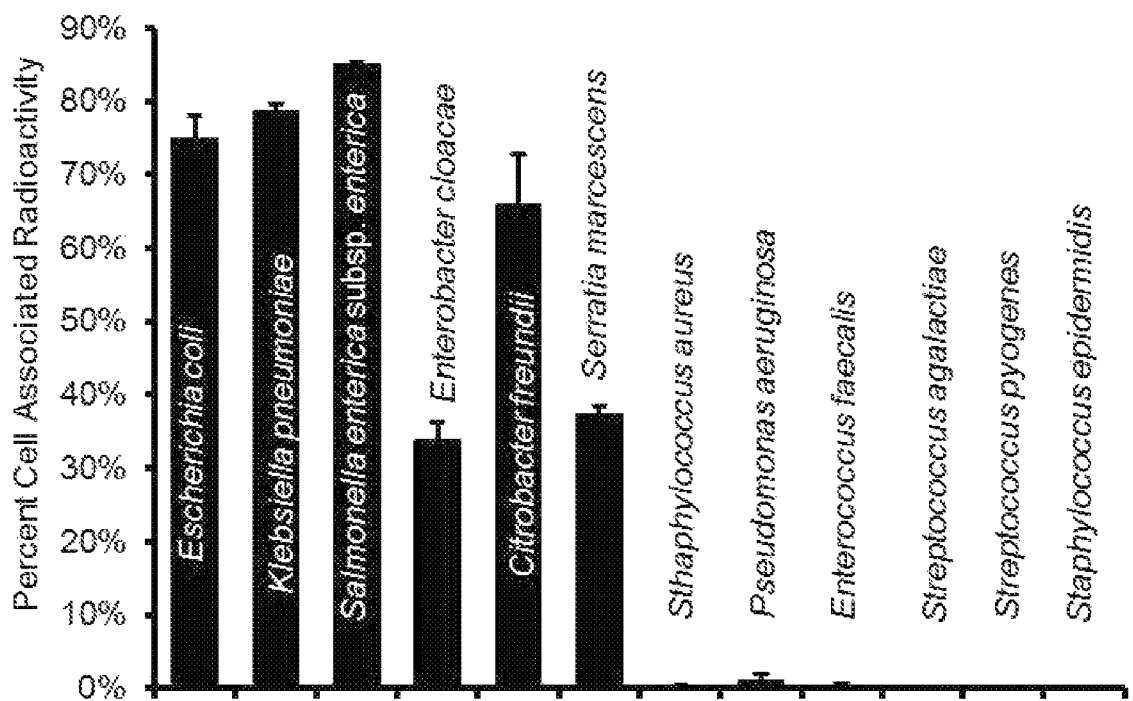
FIG. 6C is a bar graph showing that members of the Enterobacteriaceae family accumulated [$^{18}$F]FDS, whereas gram positive organisms such as *Enterococcus, Staphylococcus* and *Streptococcus* species, as well as the aerobic gram-negative rod *Pseudomonas aeruginosa* did not accumulate the probe.

To further assess the specificity of uptake, *E. coli* cultures were co-incubated with [$^{18}$F]FDS and increasing concentrations of unlabeled sorbitol (FIG. 6B). [$^{18}$F]FDS uptake was outcompeted by concentrations of sorbitol above 40 ug/ml, indicating that the accumulation of [$^{18}$F]FDS was a saturable, presumably transporter driven process. The presence of a srl gene cassette responsible for sorbitol transport, phosphorylation, and oxidation was noted within the annotated genome of *E. coli*. To predict the range of organisms capable of [$^{18}$F]FDS uptake, and therefore detection by PET, the srlD, the gene encoding *E. coli* sorbitol-6-phosphate dehydrogenase was used to query the UniProtKB database of genome sequenced bacterial species. Alignment and percentage identity was calculated using ClustalOmega. We then selected representative organisms from this panel to test for [$^{18}$F]FDS uptake (FIG. 6C). Members of the Enterobacteriaceae family accumulated [$^{18}$F]FDS, whereas gram positive organisms such as *Enterococcus, Staphylococcus* and *Streptococcus* species, as well as the aerobic gram-negative rod *Pseudomonas aeruginosa* did not accumulate the probe.

Example 5

Figures 7A, 7B:
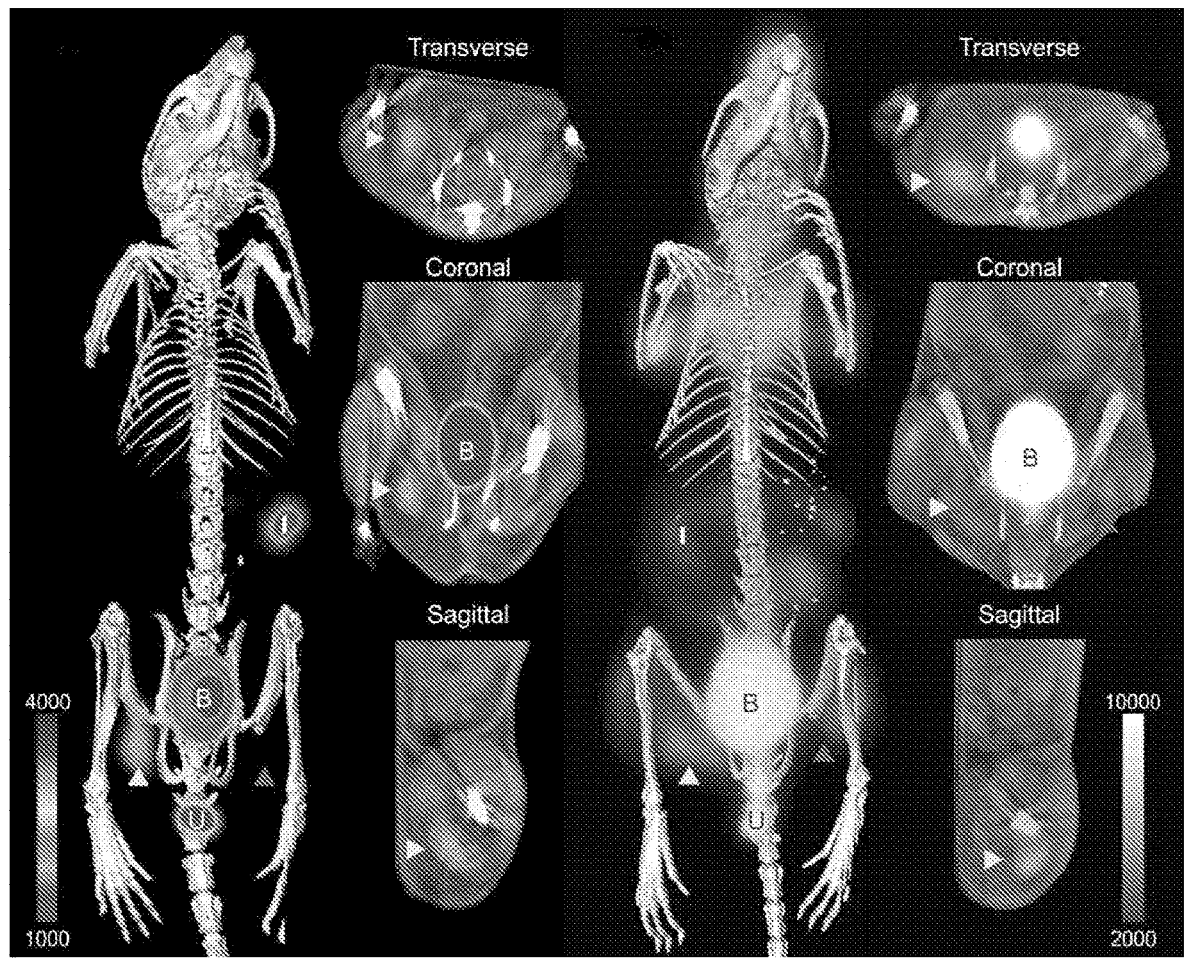
FIGS. 7A and 7B compare PET images acquired using either [$^{18}$F]FDS or [$^{18}$F]FDG. Immunosuppressed CBA/J mice were inoculated with either 1.49×10$^7$ CFU of live *E. coli* (right thighs) or an equal, heat killed dose of *E. coli* (left thighs). Imaging was performed following 8 hours of incubation, allowing the CFU count in infected right thighs to increase to 2.01×10$^9$ CFU. [$^{18}$F]FDS (7A) readily concentrated in the infected right thigh, gall bladder, intestine, and bladder as determined by CT coregistration, but not in the uninfected left thigh. [$^{18}$F]FDG (7B) produced a diffuse signal that could not differentiate the infected right thigh, from the uninfected left thigh.
Figure 7C:
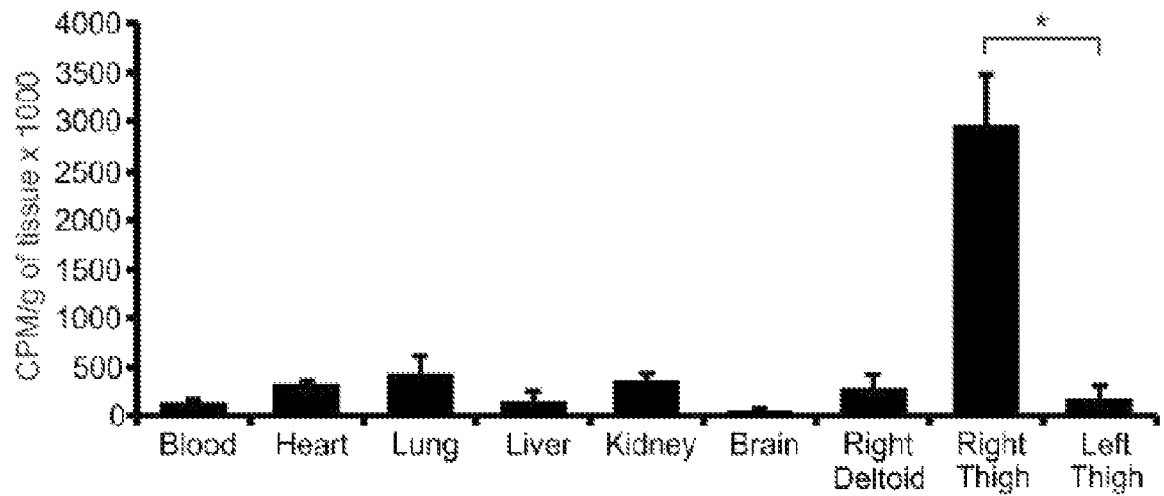
FIG. 7C is a bar graph depicting gamma counts from surgically resected tissues from the mice depicted in FIG. 7A.
Figure 7D:
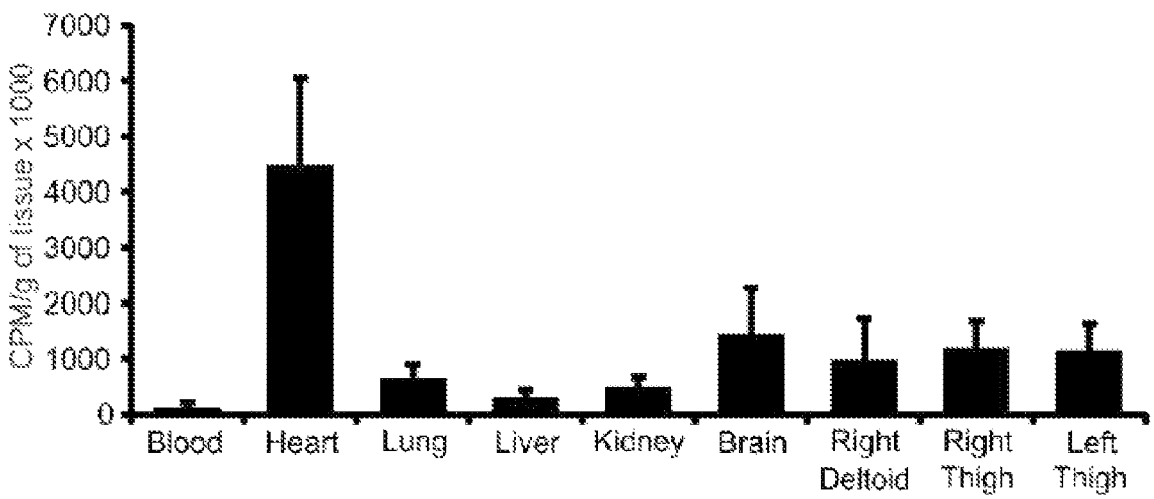
FIG. 7D is a bar graph depicting gamma counts from surgically resected tissues from the mice depicted in FIG. 7B.
Figure 7E:
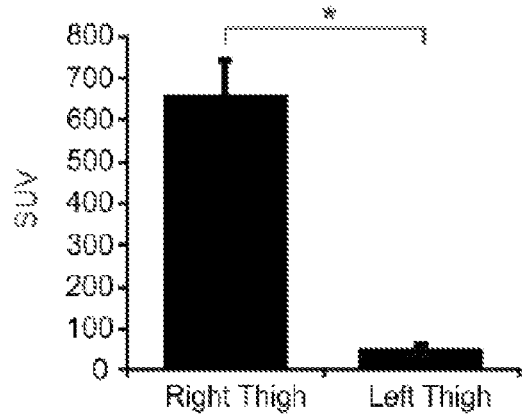
FIGS. 7E and 7F are bar graph depicting PET signal intensities from spherical regions of interest (ROIs) drawn within the thighs based upon anatomical localization by CT. [$^{18}$F]FDG did not produce a significant difference in signal intensity between right and left thighs (7F, P>0.1), whereas [$^{18}$F]FDS produced a 12-fold greater signal intensity in the infected right thigh (7E, P=0.013) versus the control left thigh.
Figure 7F:
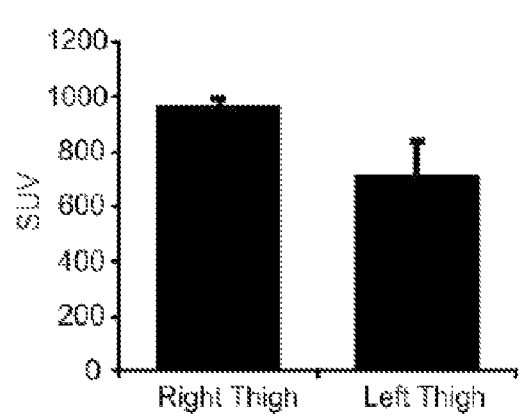

In-vivo imaging using [$^{18}$F]FDS. We next investigated whether [$^{18}$F]FDS-PET was capable of detecting infection with *E. coli* in vivo. Immunosuppressed CBA/J mice were inoculated with either 1.49×10$^7$ CFU of live *E. coli* (FIG. 7A, right thigh) or an equal, heat killed dose of *E. coli* (FIG. 7B, left thigh). Imaging was performed following 8 hours of incubation, allowing the CFU count in infected right thighs to increase to 2.01×10$^9$ CFU. [$^{18}$F]FDS readily concentrated in the infected right thigh, gall bladder, intestine, and bladder as determined by CT coregistration, but not in the left thigh (FIG. 7A). The signal to noise ratio improved over 120 minutes of recording as the probe was cleared from circulation, predominantly by the kidneys and to a minor extent by the liver into the gall bladder and intestine (data not shown). [$^{18}$F]FDG produced an intense signal in the heart and bladder, but the infected right thigh was not easily distinguishable from other skeletal muscles (FIG. 7B). To quantify the PET signal intensities, spherical regions of interest (ROIs) were drawn within the thighs based upon anatomical localization by CT (FIGS. 7E, 7F). [$^{18}$F]FDG did not produce a significant difference in signal intensity between right and left thighs (P>0.1), whereas [$^{18}$F]FDS produced a 12-fold greater signal intensity in the infected right thigh (P=0.013) versus the control left thigh. To confirm these findings, mice were sacrificed following imaging, tissues were then resected and gamma counted. Measured by this technique, a right thigh vs. left thigh uptake ratio of 16.37±4.12 (P=0.014) was noted for [$^{18}$F]FDS and 1.03±0.09 (P>0.9) for [$^{18}$F]FDG (FIGS. 7C, 7D).

Example 6

Figures 8A, 8B:
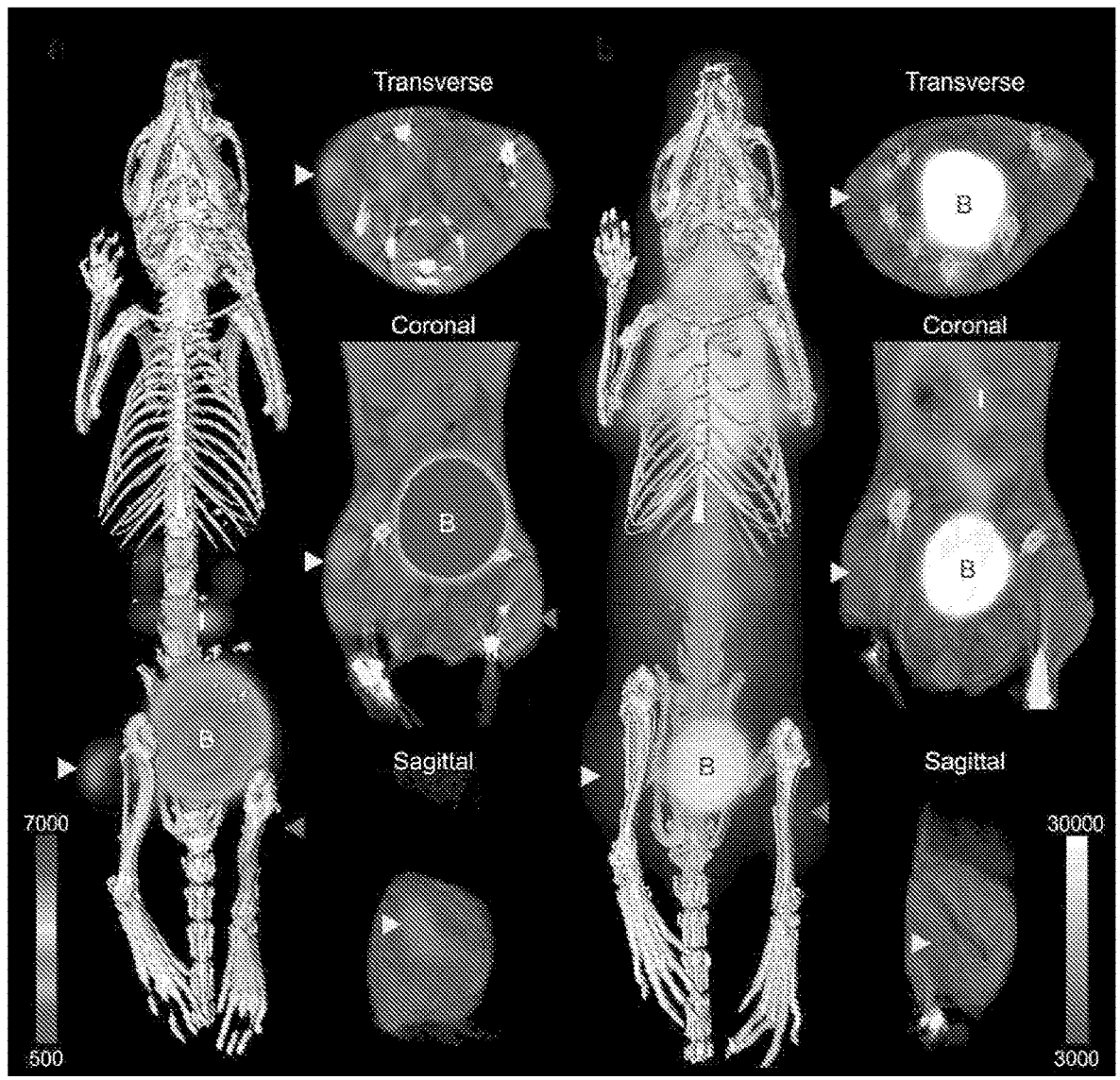
FIGS. 8A and 8B are PET images using [$^{18}$F]FDS and [$^{18}$F]FDG in the presence of mixed infections. Immunosuppressed CBA/J mice were inoculated with $7.6\times10^6$ CFU live *E. coli* (right thigh) and $1.5\times10^9$ CFU live *S. aureus* (left thigh). These mice were considerably more ill-appearing due to the added infectious burden of *S. aureus*, prompting a shorter incubation time of 6 hours prior to imaging. [$^{18}$F]FDS yielded significantly more intensity at the site of the *E. coli* infection in the right thigh (FIG. 8A) while [$^{18}$F]FDG produced a similar signal in both thighs, and was unable to differentiate *E. coli* infection from *S. aureus* infection (FIG. 8B)
Figure 8C:
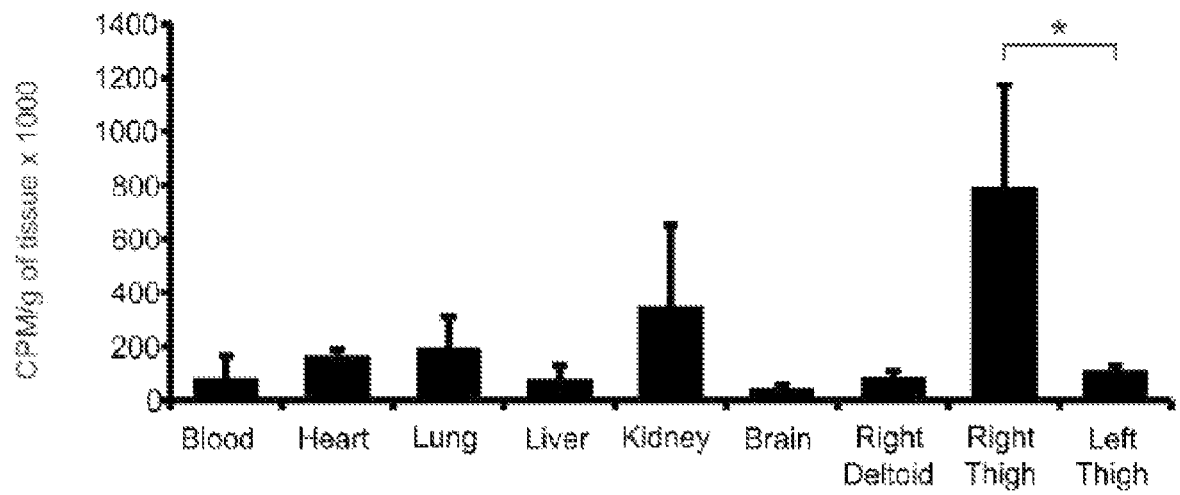
FIG. 8C is a bar graph depicting gamma counts of surgically resected tissues from the [$^{18}$F]FDS injected mouse depicted in FIG. 8A.
Figure 8D:
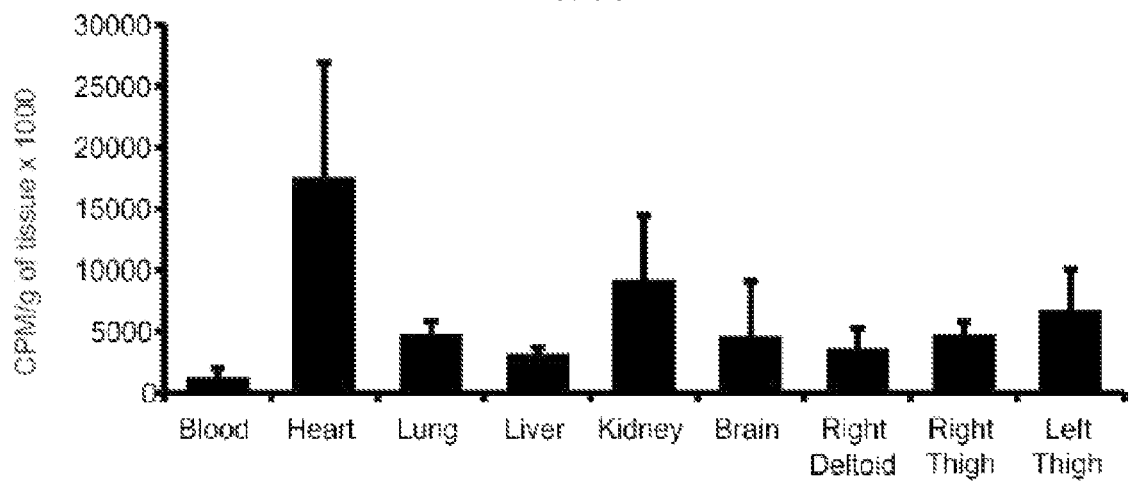
FIG. 8D is a bar graph depicting gamma counts of surgically resected tissues from the [$^{18}$F]FDG injected mouse depicted in FIG. 8B.
Figure 8E:
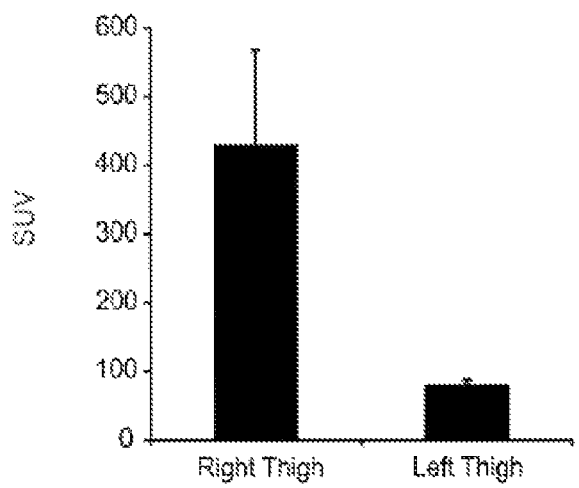
FIGS. 8E ([$^{18}$F]FDS injected) and 8F ([$^{18}$F]FDG injected) are bar graphs from mice in FIGS. 8A and 8B respectively, depicting PET signal intensities from spherical regions of interest (ROIs) drawn within the thighs based upon anatomical localization by CT.
Figure 8F:
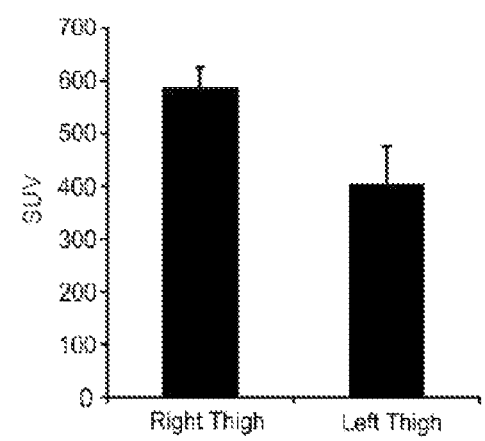

To next test the selectivity of FDS in the presence of mixed infections, immunosuppressed CBA/J mice were inoculated with 7.6×10$^6$ CFU live *E. coli* (right thigh) and 1.5×10$^9$ CFU live *S. aureus* (left thigh). These mice were considerably more ill-appearing due to the added infectious burden of *S. aureus*, prompting a shorter incubation time of 6 hours prior to imaging. [$^{18}$F]FDS yielded significantly more intensity at the site of the *E. coli* infection in the left thigh (FIGS. 8A, 8E) (P=0.1254) while [$^{18}$F]FDG produced a similar signal by imaging (FIGS. 8B, 8F) (P=0.2470). Upon tissue resection, the right thigh vs. left thigh ratios of radioactivity were noted to be 6.94±26.33 (P=0.002) and 0.69±0.31 (P=0.328) for [$^{18}$F]FDS and [$^{18}$F]FDG, respectively (FIGS. 8C, 8D). Whereas the myositis model was selected for the ability to compare infection versus inflammation between thighs we wished to test a second pathogen in a more clinically relevant model.

Example 7

Figure 9A:
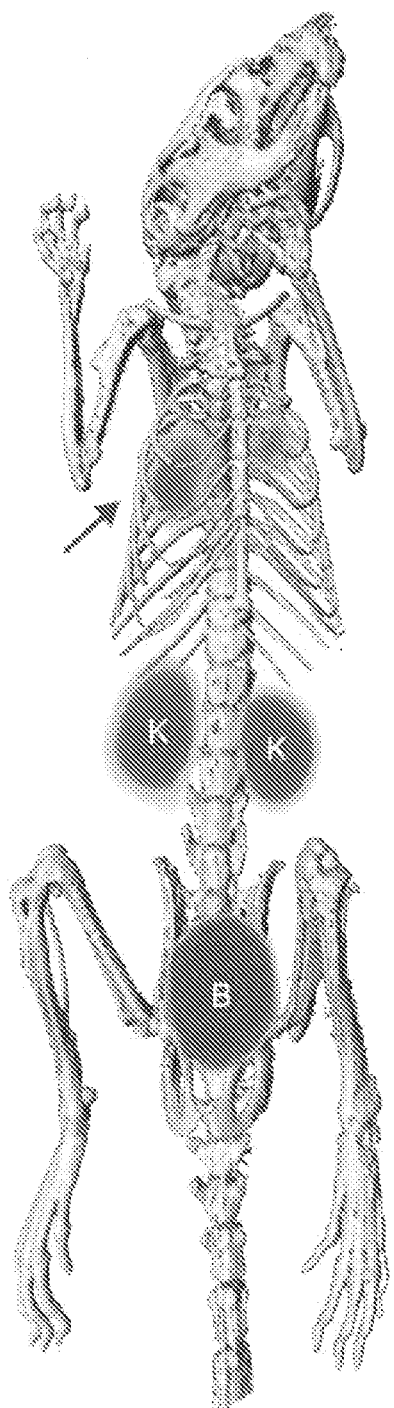
FIG. 9A is a graphical depiction of PET signal intensity of immunosuppressed CBA/J mice inoculated with $3\times10^6$ CFU *K. pneumoniae* by intratracheal instillation. The areas of lung infiltration coregistered with foci of PET signal intensity.
Figure 9B:
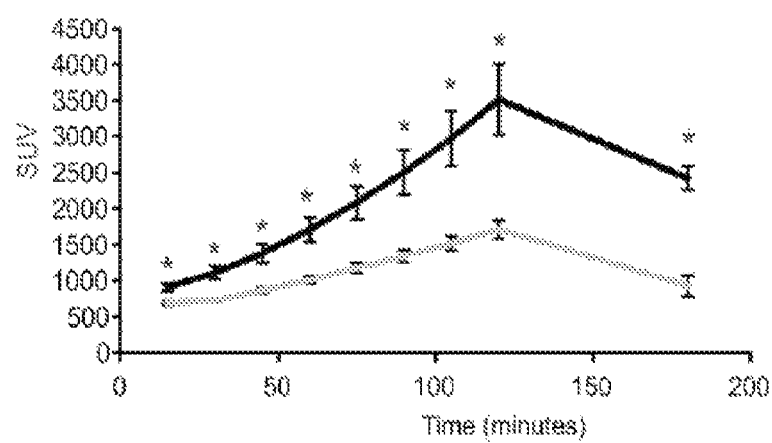
FIG. 9B is a graph showing the optimum time for detection. 18.5 MBq [$^{18}$F]FDS was injected, and images were collected by dynamic windows of 15 minutes over the course of 180 minutes.
Figure 9C:
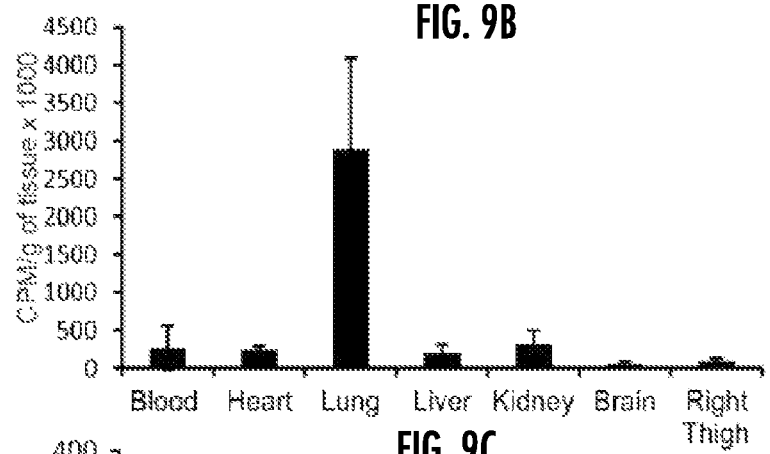
FIG. 9C is a bar graph depicting gamma counts of various tissues from mice given a pulmonary infection with *K. pneumoniae*. A whole lung homogenization followed by solid agar plating recovered $2.31\times10^9$ CFU. The lung vs. blood gamma count ratio was 10.89±4.09.
Figure 9D:
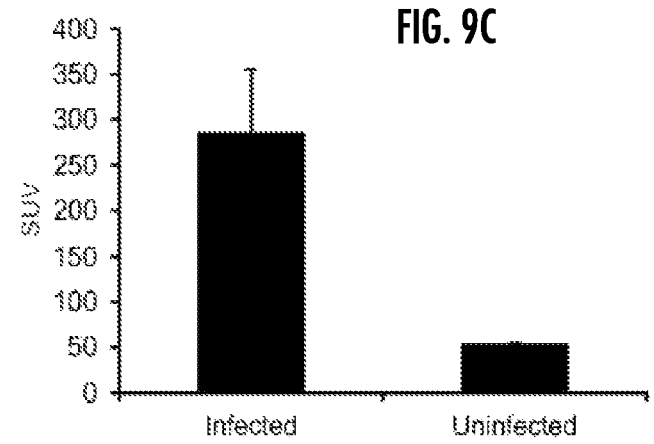
FIG. 9D is a bar graph depicting the PET signal differences between infected and uninfected tissue based on ROIs drawn over diseased and normal lung tissue.

We next examined whether [$^{18}$F]FDS could detect pulmonary infection associated with *K. pneumoniae*, the causative agent of Friedlander's disease. Immunosuppressed CBA/J mice inoculated with 3×10$^6$ CFU by intratracheal instillation developed pulmonary infiltrates observed by CT over the course of 5 days of incubation. As expected, the areas of lung infiltration coregistered with foci of PET signal intensity (FIG. 9A). To optimize the sensitivity of detection, 18.5 MBq [$^{18}$F]FDS was injected, and images were collected by dynamic windows of 15 minutes over the course of 180 minutes (FIG. 9B). ROIs were drawn over infiltrated and normal lung tissue and to calculate a ratio of standardized uptake values of 5.02±66.33 (data not shown). Whole lung homogenization followed by solid agar plating recovered 2.31×10$^9$ CFU with a lung vs. blood gamma count ratio of 10.89±4.09 (FIG. 9C).

Example 8

In order to confirm the feasibility of $^{18}$F labeled PABA for detection of microorganisms using PET imaging, fluorinated derivatives of PABA labeled with $^3$H were used to test for intracellular accumulation in *S. aureus, E. coli*, and *M. tuberculosis*.

*Mycobacterium tuberculosis* cultures were incubated with [$^3$H]-PABA, [$^3$H]-2-F-PABA and [$^3$H]-3-F-PABA according to the protocols in the previous examples. High intracellular uptake was found in *M. tb* after 18 hours of incubation: PABA (58.5%), 2-F-PABA (29.4%) and 3-F-PABA (11.2%). In addition, there was no significant intracellular uptake (<1%) of PABA, 2-F-PABA or 3-F-PABA in eukaryotic J774 macrophages, Human Brain Microvascular Endothelial Cells (HBMEC) and WEHI 164 fibroblasts.

Furthermore, preliminary data on [$^3$H]-PABA, [$^3$H]-2-F-PABA uptake in various bacterial pathogens gave positive results (>5% of selective intracellular uptake) for *Escherichia coli, Staphylococcus aureus, Klebsiella pneumoniae, Enterobacter cloacae, Enterococcus faecalis, Streptococcus pyogenes* and *Serratia marcescens*.

We next investigated whether [$^3$H]-2-F-PABA was capable of detecting infection with *S. aureus* in vivo. Immunosuppressed CBA/J mice were inoculated with either live *S. aureus* (right thigh) or 50 µg of LPS (left thigh). [$^3$H]-2-F-PABA was injected IV using a tail vein catheter. Mice were sacrificed following injection, tissues were then resected and radiotracer uptake measured by scintillation counting. Measured by this technique, [$^3$H]-2-F-PABA had a right thigh vs. left thigh uptake ratio of 2.62±0.98 (P<0.05). Thus, demonstrating the feasibility of $^{18}$F labeled 2-F-PABA for imaging gram positive infections.

Example 9

In order to test the feasibility of $^{18}$F labeled mannitol for detection of gram positive organisms using PET imaging, a fluorinated derivative of mannitol (2-fluoro-mannitol) labeled with $^3$H was used to test the uptake characteristics of the probe. We first incubated *S. aureus* for 30 minutes with 5 and 10 mM of glucose in the presence of $^{14}$C-mannitol and found an intracellular uptake of 33% and 30% respectively as compared to 53.5% without any glucose in the media. Thus indicating the presence of specific mannitol transporters in *S. aureus*.

An in silico analysis for genes encoding mannitol specific transporters was performed, with positive results for multiple bacteria including *S. aureus, E. coli, S. mutans*, suggesting that 2-fluoromannitol can detect a broad range of clinically significant pathogens Experiments were then performed showing intracellular uptake of [$^3$H]-2-F-mannitol after 120 minutes of incubation was 8.98%. Moreover, it was found that if [$^3$H]-2-F-mannitol was incubated with 0.2 mM of cold mannitol amplified its intracellular uptake to 31.08% due to the induction of sugar transporters. Mannitol is an FDA approved diuretic, and the dose required for diuresis is similar the dose observed to amplify 2-Fluoromannitol uptake. Thus, $^{18}$F labeled 2-F-mannitol is an interesting probe for imaging infections that may prove to be extremely sensitive for detecting small numbers of microbes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of detecting the presence of live infectious Gram negative bacteria of the family Enterobacteriaceae at an infected site in the body of a mammalian host comprising:
    (a) administering to the mammalian host a therapeutically effective amount of a labeled substrate comprising $^{18}$F-fluorodeoxysorbitol (FDS);
    (b) allowing a sufficient period of time for the infectious Gram negative bacteria to take up the labeled substrate; and
    (c) detecting the labeled substrate taken up by the live infectious gram negative bacteria at the infected site in the body of the mammalian host by in vivo imaging, wherein the labeled substrate is taken up by the live infectious gram negative bacteria at a greater intensity compared to the normal cells or inflamed cells of the mammalian host.

2. The method of claim 1, wherein the in vivo imaging is positron emission tomography (PET) imaging.

* * * * *